US010816556B2

(12) United States Patent
Vertes et al.

(10) Patent No.: US 10,816,556 B2
(45) Date of Patent: Oct. 27, 2020

(54) TAILORED NANOPOST ARRAYS (NAPA) FOR LASER DESORPTION IONIZATION IN MASS SPECTROMETRY

(71) Applicants: The George Washington University, Washington, DC (US); UT-Battelle, LLC, Oak Ridge, TN (US)

(72) Inventors: Akos Vertes, Reston, VA (US); Bennett N. Walker, Washington, DC (US); Jessica A. Stolee, Washington, DC (US); Scott T. Retterer, Oak Ridge, TN (US)

(73) Assignees: The George Washington University, Washington, DC (US); UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 16/813,490

(22) Filed: Mar. 9, 2020

(65) Prior Publication Data
US 2020/0292557 A1    Sep. 17, 2020

Related U.S. Application Data

(62) Division of application No. 15/270,440, filed on Sep. 20, 2016, now Pat. No. 10,585,104, which is a division of application No. 12/755,769, filed on Apr. 7, 2010, now Pat. No. 9,490,113.

(60) Provisional application No. 61/167,442, filed on Apr. 7, 2009.

(51) Int. Cl.
*G01N 33/68* (2006.01)
*H01J 49/04* (2006.01)
*G01N 33/483* (2006.01)
*H01J 49/00* (2006.01)

(52) U.S. Cl.
CPC ..... *G01N 33/6851* (2013.01); *G01N 33/4833* (2013.01); *H01J 49/0418* (2013.01); *G01N 33/6848* (2013.01); *H01J 49/0031* (2013.01); *Y02E 10/52* (2013.01)

(58) Field of Classification Search
CPC .......... G01N 33/4833; G01N 33/6848; G01N 33/6851; H01J 49/0418
See application file for complete search history.

(56) References Cited

U.S. PATENT DOCUMENTS

2009/0321633 A1    12/2009 Blick

OTHER PUBLICATIONS

Lee et al., Appl. Phys. A, 79:2027-2031; 2004.
Nallani et al., Proc. SPIE 5116, Smart Sensors, Actuators, and MEMS, Apr. 24, 2003.

*Primary Examiner* — Jeremy C Flinders
(74) *Attorney, Agent, or Firm* — Blank Rome LLP

(57) ABSTRACT

The production and use of semiconducting nanopost arrays made by nanofabrication is described herein. These nanopost arrays (NAPA) provide improved laser ionization yields and controllable fragmentation with switching or modulation capabilities for mass spectrometric detection and identification of samples deposited on them.

17 Claims, 15 Drawing Sheets

TAILORED NANOPOST ARRAYS (NAPA) FOR LASER DESORPTION IONIZATION IN MASS SPECTROMETRY

STATEMENT OF PRIORITY

This application is a divisional application of U.S. patent application Ser. No. 15/270,440, filed Sep. 20, 2016, now U.S. Pat. No. 10,585,104, which is a divisional application of U.S. patent application Ser. No. 12/755,769, filed Apr. 7, 2010, now U.S. Pat. No. 9,490,113, issued Nov. 8, 2016, which claims priority to U.S. Provisional Patent Application No. 61/167,442, filed Apr. 7, 2009. The disclosures of which are hereby incorporated by reference.

STATEMENT REGARDING FEDERALLY SPONSORED RESEARCH

This invention was made with government support under grant number DEFG02-01ER15129 from the Department of Energy. The U.S. Government has certain rights in this invention.

BACKGROUND OF THE INVENTION

Field of the Invention

The field of the invention is mass spectrometry (MS), and more specifically nanoposts and nanopost arrays having specific geometries for improved ion yield in laser desorption ionization mass spectrometry.

Description of the Related Art

Laser desorption ionization mass spectrometry (LDI-MS) of organic molecules and biomolecules provides chemical analysis with great selectivity and sensitivity. Presently available methods generally rely on the interaction of laser radiation with a matrix material or with nanoporous substrates for the production of ions. Examples of these techniques include matrix-assisted laser desorption ionization (MALDI), desorption ionization on silicon (DIOS), and nanostructure-initiator mass spectrometry (NIMS).

From laser shot to laser shot, these methods exhibit spontaneous fluctuations in ion yields. Ion yields can only be controlled by adjusting the fluence delivered to the surface.

However, conventional soft laser desorption ionization by MALDI requires a matrix for desorption, complicating sample preparation and adding spectral interferences. Further, laser-induced silicon microcolumn arrays (LISMA) do not provide a sufficiently wide range of geometries and thus cannot enable a tailored platform for laser desorption ionization MS. Additionally, in MALDI the surface chemistry cannot be conveniently altered and thus cannot provide additional control over the properties of the produced ions. Lastly, the prior art does not adequately address the use of microcolumns or nanoposts that are integrated with microfluidic devices.

Highly confined electromagnetic fields play an important role in the interaction of laser radiation with nano structures. Near-field optics show great potential in manipulating light on a sub-micron or even on the molecular scale. Nanophotonics takes advantage of structures that exhibit features commensurate with the wavelength of the radiation. Among others it has been utilized for nanoparticle detection, for the patterning of biomolecules and for creating materials with unique optical properties. The latter include LISMA, produced by ultrafast laser processing of silicon surfaces, and are known to have uniformly high absorptance in the 0.2-2.4 µm wavelength range as well as superhydrophobic properties.

At sufficiently high laser intensities, the molecules adsorbed on these nanostructures undergo desorption, ionization and eventually exhibit unimolecular decomposition. The resulting ion fragmentation patterns can be used for structure elucidation in MS. Accordingly, manipulation of ion production from biomolecules with photonic structures (i.e., photonic ion sources) based on the laser light-nanostructure interaction, is provided herein on nanofabricated and tailored nanopost arrays (NAPA).

Photonic ion sources based on array-type nanostructures, such as LISMA, can serve as platforms for LDI-MS for the detection and identification of various organic and biomolecules. Compared to conventional LDI-MS ion sources, e.g., MALDI, DIOS and NIMS, nanophotonic ion sources couple the laser energy to the nanostructures via a fundamentally different mechanism due to the quasiperiodic or periodic and oriented nature of the arrays. Nanophotonic ion sources show a dramatic disparity in the efficiency of ion production depending on the polarization and the angle of incidence of the laser. When the electric field of the radiation has a component that is parallel to the column axes (e. g., p-polarized beam) the desorption and ionization processes are efficient, whereas in case they are perpendicular (s-polarized beam) minimal or no ion production is observed. In addition, LISMA exhibit a strong directionality in ion production. The ion yield as a function of the incidence angle of an unpolarized laser beam decreases and ultimately vanishes as the incidence angle approaches 0°. This strong directionality in ion production is also a unique feature of NAPA.

Photonic ion sources, such as LISMA, rely on the quasi-periodic or periodic and oriented nature of the nanostructures with dimensions commensurate with the wavelength of the laser light. These photonic ion sources rely on unique nanophotonic interactions (e.g., near-field effects, plume confinement, and interference effects) between the electromagnetic radiation and the nanostructure on one hand, and the interaction of both with the surface-deposited sample molecules, on the other. These devices exhibit a strong control of ion production by varying laser radiation properties other than simple pulse energy, mainly through changes in the angle of incidence and the plane of polarization of the laser radiation. Tailoring the structural parameters of photonic ion sources (e.g., column diameter, column height and periodicity) enable further control over coupling the laser energy into the structure on a micro and nano scale. Combination of nanophotonic ion sources with miniaturized mass analyzers can lead to the development of integrated miniaturized mass spectrometers and analytical sensors.

SUMMARY OF THE INVENTION

It is an object of the present invention to provide methods for making nanopost arrays for matrix-free analysis of a sample by mass spectrometry by generating a mask pattern for a nanopost array arrangement having specific properties by computer aided design, writing the mask pattern onto a substrate to form columnar structures and developing said columnar structures to a specific height. These processes rely on nanofabrication techniques that are well known in the art. The nanopost arrays may have specific characteristics that allow for increased ion production and molecular fragmentation.

It is a further object of the present invention to provide nanopost arrays made using the methods of the present invention. The nanopost arrays may be used for sample ionization and fragmentation during mass spectrometry analysis.

It is a further object of the present invention to provide mass spectrometry systems containing the nanopost arrays of the present invention. The mass spectrometry systems of the present invention include mass spectrometers for analysis of molecules as are well known in the art.

It is a further object of the present invention to provide sensor devices containing the nanopost arrays of the present invention. The sensor devices may be used in the detection of a wide variety of samples, from small chemical molecules, up to large molecules, biomolecules and whole cells.

It is a further object of the present invention to provide a method for the analysis of a forensic sample by depositing the forensic sample onto a nanopost array of the present invention, desorbing the sample and detecting ions produced by the sample by mass spectrometry.

It is a further object of the present invention to provide a method for the analysis of an environmental sample by depositing the environmental sample onto a nanopost array of the present invention, desorbing the sample and detecting ions produced by the sample by mass spectrometry.

It is a further object of the present invention to provide a method for the analysis of a biomedical sample by depositing the biomedical sample onto a nanopost array of the present invention, desorbing the sample and detecting ions produced by the sample by mass spectrometry.

It is a further object of the present invention to provide a method for the analysis of a synthetic organic sample by depositing the synthetic organic sample onto a nanopost array of the present invention, desorbing the sample and detecting ions produced by the sample by mass spectrometry.

It is a still further object of the present invention to provide a method for harvesting solar energy by subjecting a nanopost array of the present invention having columnar structures with an electromagnetic radiation-capture coating to solar radiation and withdrawing the electrical charge produced by the electronically converted coating.

Figure 4A:
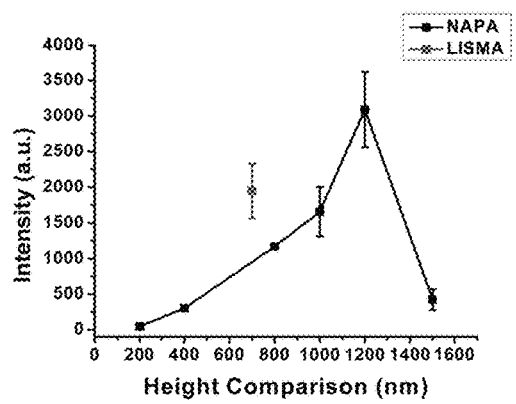
FIG. 4A shows the relationship between the ion yield for substance P and NAPA dimensions, such as post height for 200 nm post diameter and 450 nm periodicity.
Figure 4B:
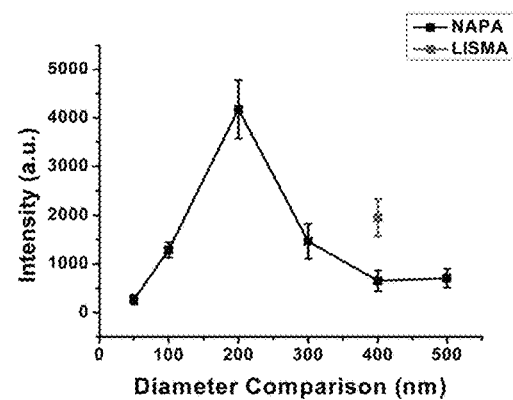
FIG. 4B shows a post diameter for 1000 nm post height and 350 nm trough width.

Points in red (not connected) in FIGS. 4A and 4B show the corresponding values for LISMA.

Figure 5:
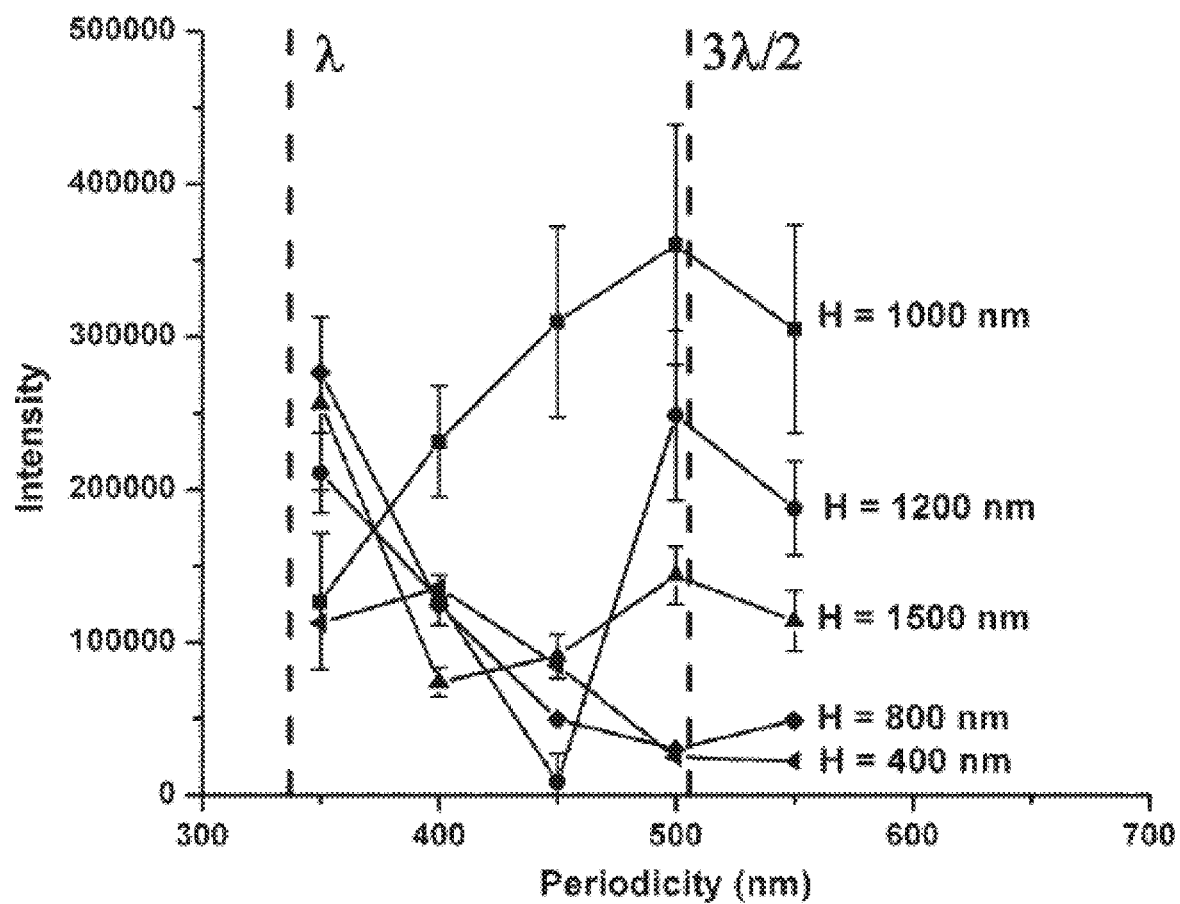

FIG. 5 shows ion yields for substance P as a function of NAPA periodicity, P, for five different post heights (H=400, 800, 1000, 1200 and 1500 nm). The post diameters are fixed at D=100 nm. The H=800, 1200 and 1500 nm posts show a maximum in ion yield at P=~λ=337 nm, i.e., when the periodicity is equal to the laser wavelength, λ. The arrays made of longer posts, H=1000, 1200 and 1500 nm, also show a maximum in ion yield at P=~3λ/2=505 nm.

Figure 6:
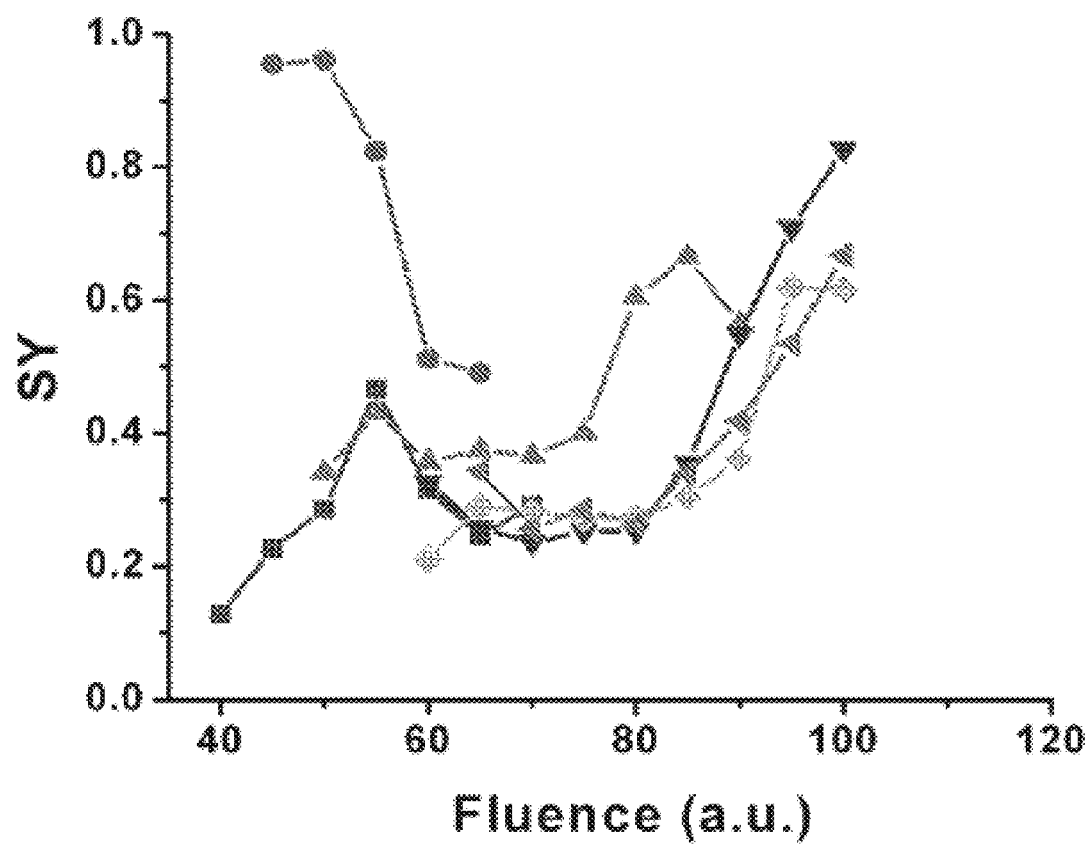

FIG. 6 show survival yields of 4-methyl-benzylpyridinium ions (4M, critical energy=1.6 eV) desorbed from NAPA with 250 nm trough widths, 1000 nm post heights, and various post diameters: 50 nm (■), 100 nm (●), 200 (▲), 300 (▼), 400 (♦), and 500 (◄). This thermometer ion (TI) desorbed from NAPA with post diameters of 100 nm exhibited decreasing survival yields as the fluence was increased whereas TIs desorbed from NAPA with larger post diameters had increasing survival yields as the fluence was increased.

Figure 7A:
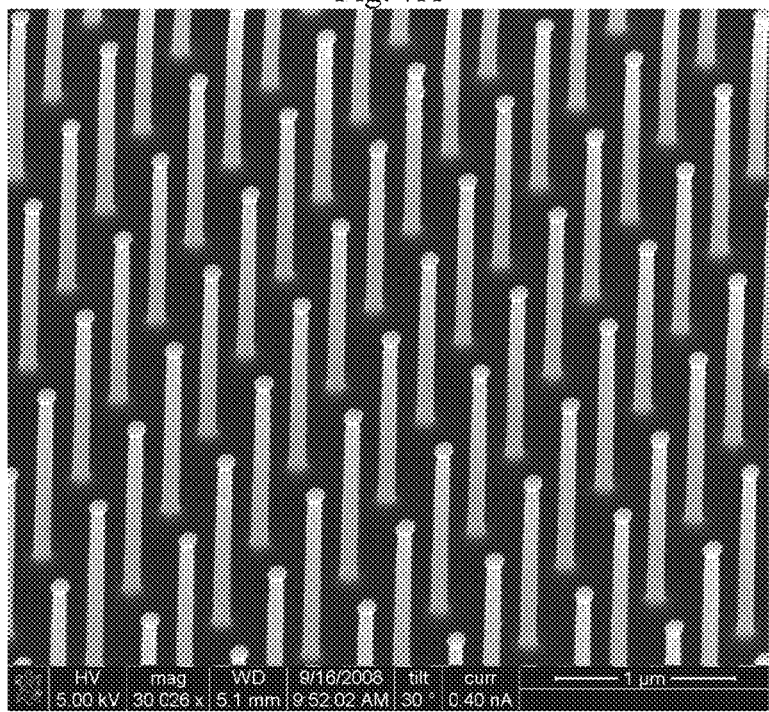

FIG. 7A shows slender nanoposts with 100 nm diameter before exposure to the desorption laser pulse.

Figure 7B:
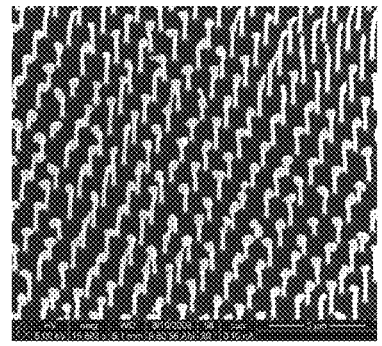
Figure 7C:
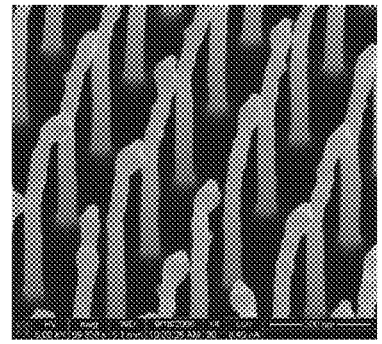

FIGS. 7B and 7C show exposure of these thin posts to a high fluence desorption laser pulse results in the deformation of nanoposts due to transient melting. Such melting and deformation was not observed for posts of larger diameter.

Figure 8:
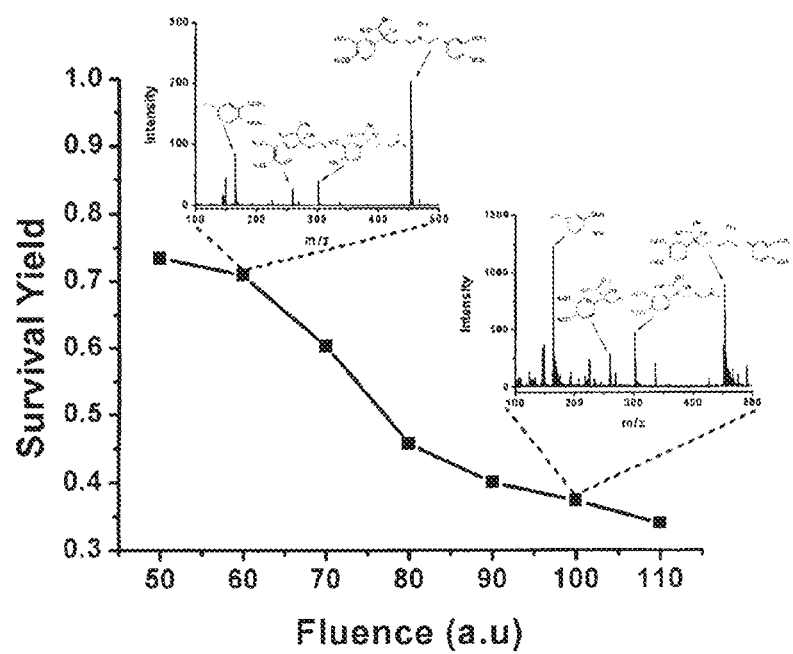

FIG. 8 shows the fluence of the desorption laser increases, the survival yield of ions from an organic molecule (verapamil) on NAPA (D=200 nm, H=1000 nm and P=500 nm) gradually decreases. Insets in the figure are the spectra at two selected fluence levels.

Figure 9:
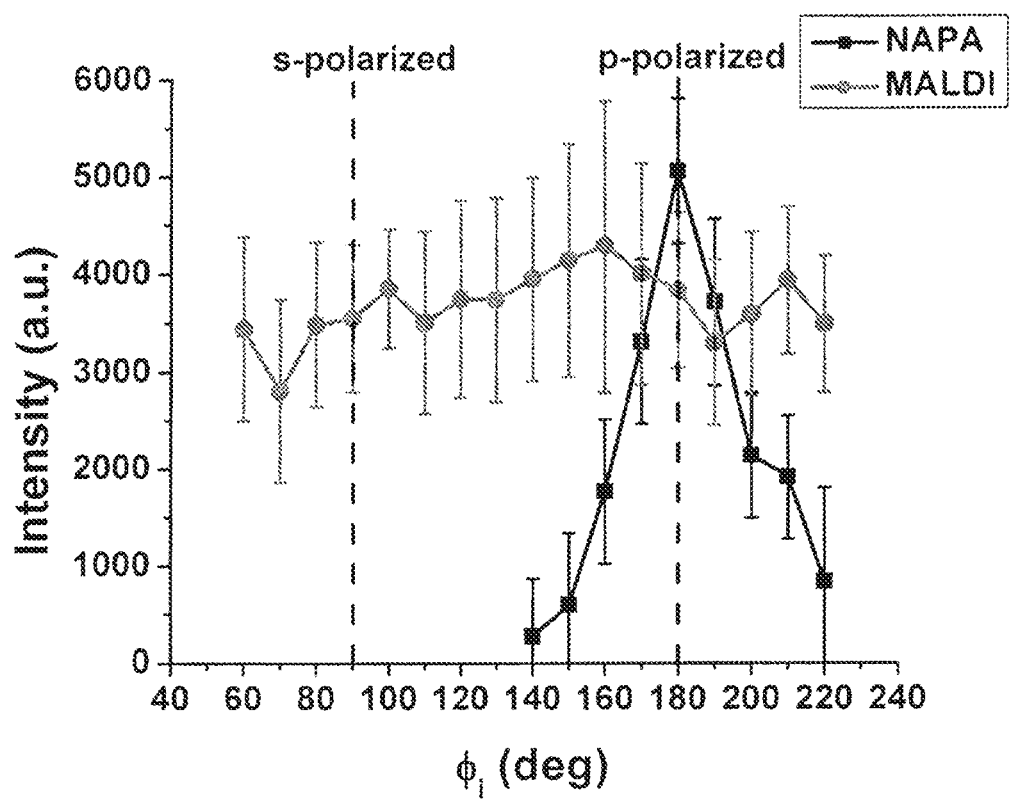

FIG. 9 shows anion yield as a function of the angle between the plane of polarization and the axes of the posts for NAPA (squares) (D=200 nm, H=1000 nm and P=500 nm) and for MALDI (circles) at constant fluence.

Figure 10A:
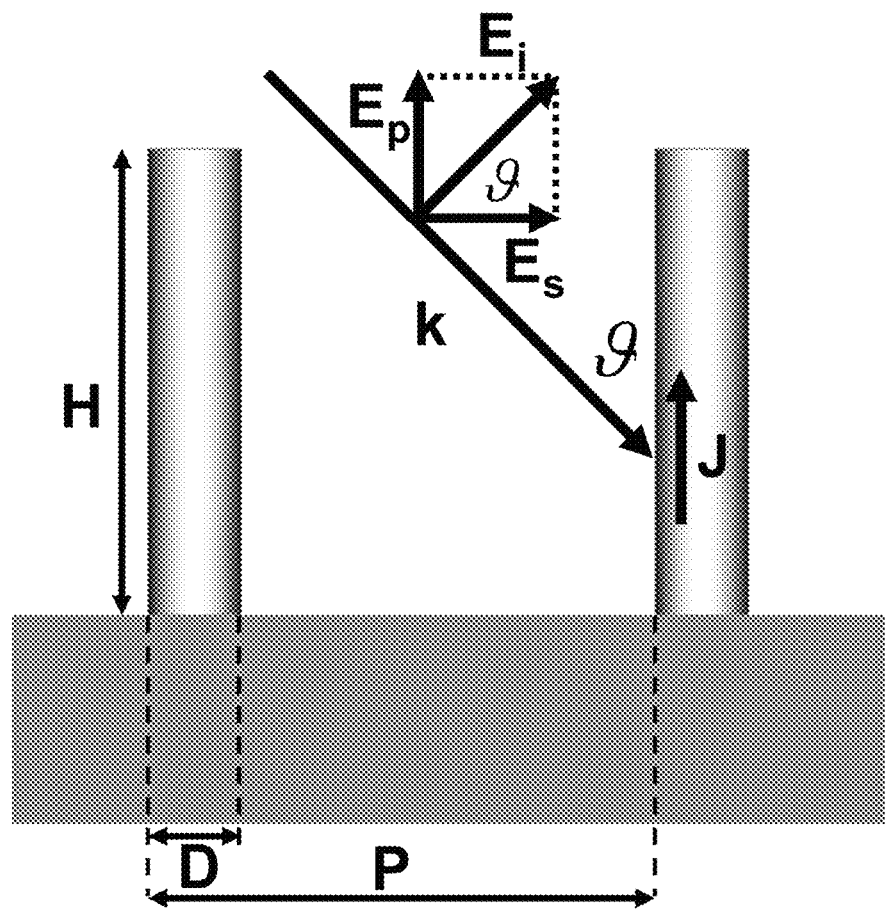

FIG. 10A shows the schematic of NAPA with post height, H, diameter, D, and periodicity, P, indicates the relationship between the electric field vector of the incident laser beam propagating in k direction, $E_i$, its orthogonal projections, and the current, J, induced in the post.

Figure 10B:
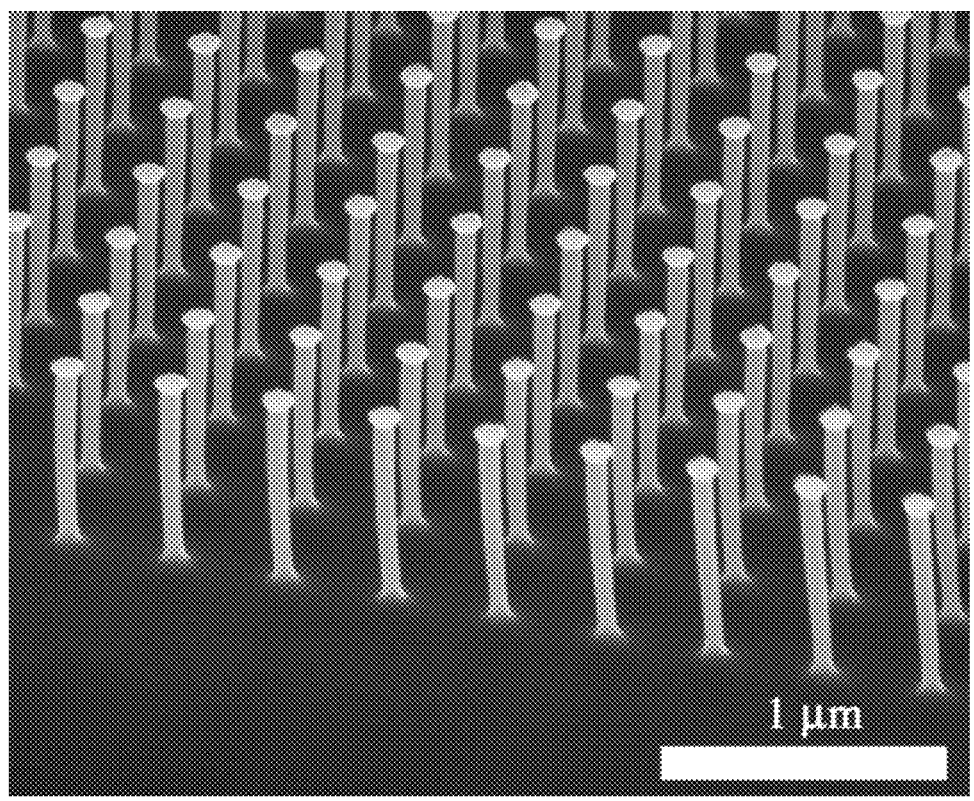

FIG. 10B shows the scanning electron microscope image of a NAPA segment with D=100 nm, H=1,000 nm and P=350 nm shows uniform periodicity and height. The posts have vertical walls with minimum tapering.

Figure 11A:
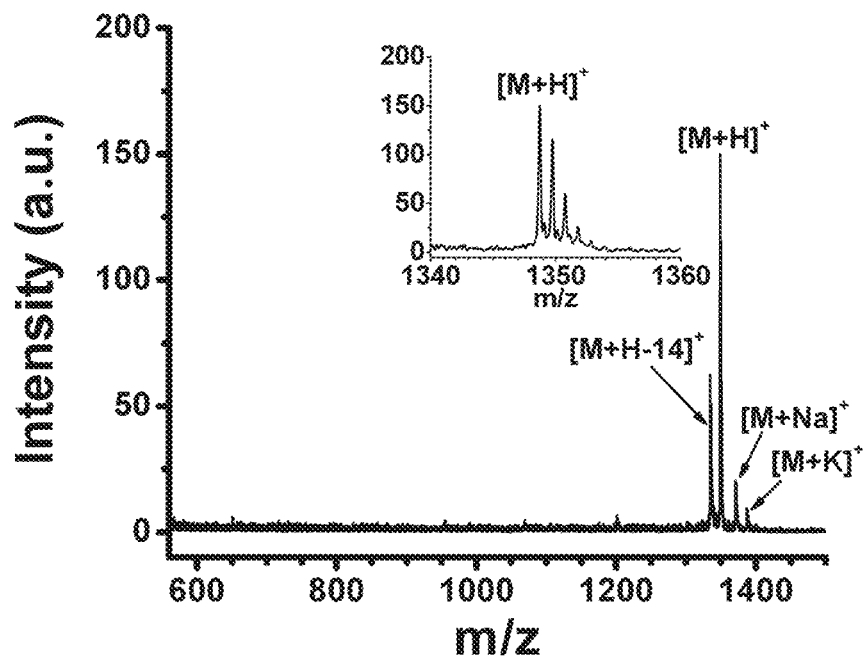

FIG. 11A shows the molecular ions in the mass spectrum of substance P produced on NAPA at low laser fluences. The inset shows the $[M+H]^+$ isotope distribution that corresponds to the calculated pattern.

Figure 11B:
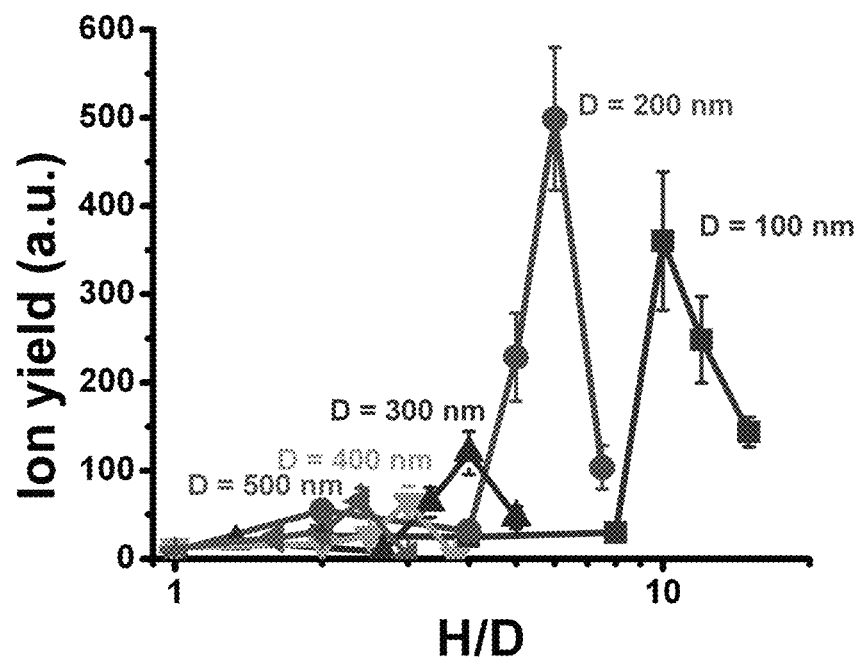

FIG. 11B shows substance P ion yields as a function of post aspect ratios show strong maxima for slender posts.

Figure 11C:
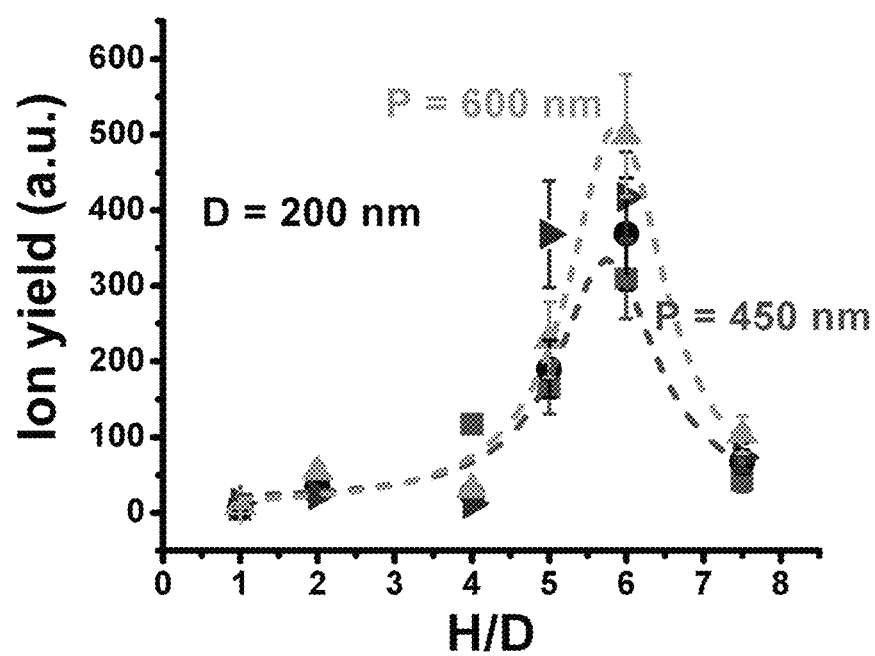

FIG. 11C shows a given diameter (D=200 nm), at the optimum aspect ratio, H/D=6, increasing periodicity, P=450 nm (■), 500 nm (●), 550 nm (►), and 600 nm (▲), results in higher ion yields. Lorentzian fits for P=450 and 600 nm represent the data with $R^2$=0.94 and 0.98 regression coefficients, respectively.

Figure 12:
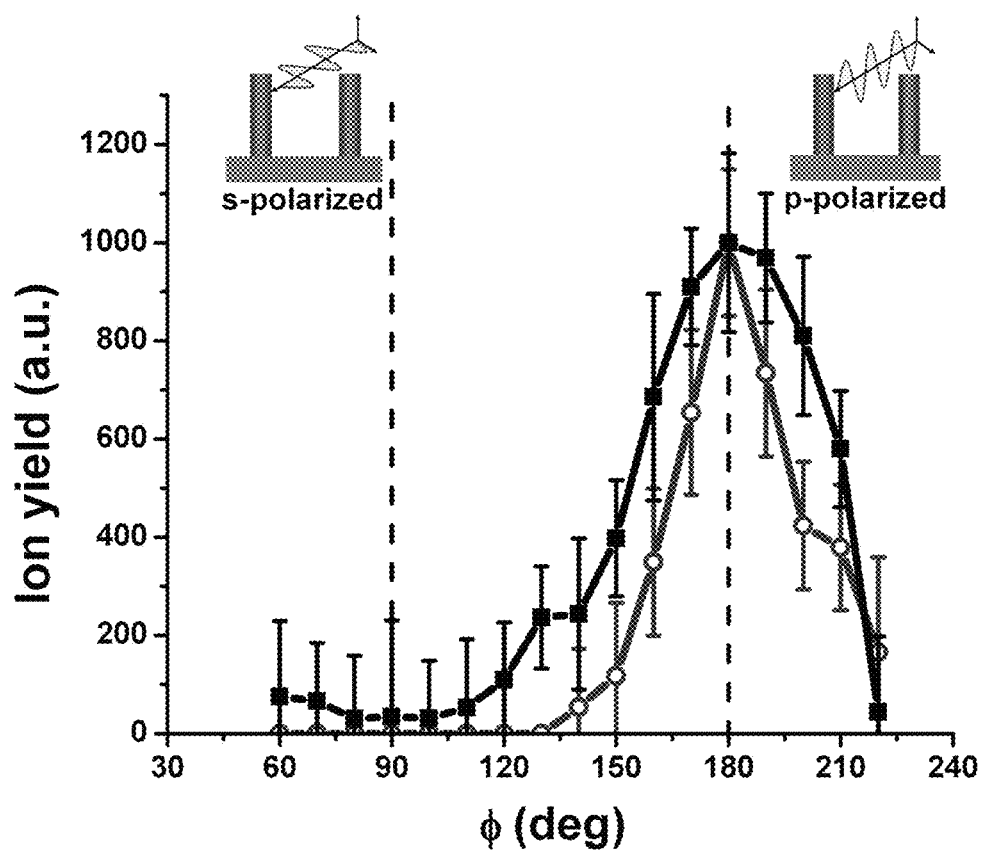

FIG. 12 shows normalized ion yields of verapamil (■) and bradykinin (○) as a function of polarization angle, ϕ, at a constant fluence (24 mJ/cm$^2$). Ion production seems to be a threshold process.

Figure 13:
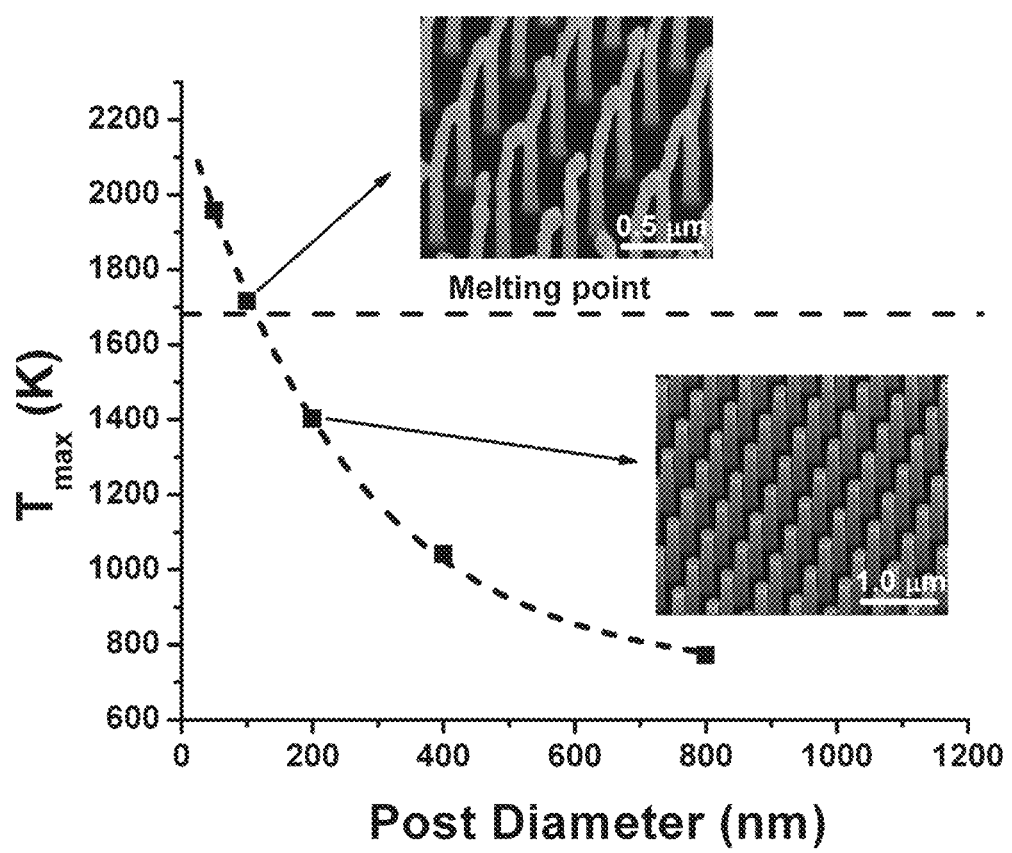

FIG. 13 shows after irradiation by a τ=5 ns laser pulse of 6×10$^6$ W/cm$^2$ power density, calculated silicon nanopost surface temperatures show a strong dependence on the post diameter in the sub-micrometer range. The SEM images in the insets indicate that posts with ~100 nm diameter exhibit signs of transient melting.

DETAILED DESCRIPTION OF THE INVENTION

Abbreviations/Definitions/Guides

LDI-MS—Laser Desorption Ionization Mass Spectrometry.

MALDI—Matrix-Assisted Laser Desorption Ionization.

DIOS—Desorption Ionization on Silicon.

NIMS—Nanostructure Initiator Mass Spectrometry.

LISMA—Laser-Induced Silicon Microcolumn Array. LISMA is a quasi-periodic structure, where the laser produced microcolumns are oriented outward of the silicon wafer surface.

NAPA—Nanopost Array.

NANOPOSTS—nanoscale columnar structures made of, e.g., silicon with dimensions that do not vary substantially across an array. For example, a nanopost array that has columns having a height of 1200 nm (±120 nm), a diameter of 200 nm (±20 nm) and a periodicity of 600 nm (±60 nm). Uniformity may be defined, individually or in combination, by the height, diameter, or periodicity/trough width of the nanostructure. Uniformity from nanofabrication techniques is in favorable contrast to nanostructures made by other methods, e.g., laser induced nanostructures.

SLDI—Soft Laser Desorption Ionization

NANOFABRICATION—the use of nanolithography, optionally in combination with reactive ion etching (RIE), to create nanostructures such as NAPA.

NANOLITHOGRAPHY—masked and maskless nanolithographic processes.

MASKLESS NANOLITHOGRAPHY is where a focused radiation beam is used to write an image directly, pixel by pixel onto a photoresist. Maskless nanolithography includes, without limitation, e-beam lithography, focused ion beam, optical, and probe tip/dip-pen.

MASKED NANOLITHOGRAPHY uses a radiation beam to transfer a pattern from a photomask to a sensitive chemical (photoresist, or simply "resist") on the substrate. A series of chemical treatments then engraves the exposure pattern into the material underneath the photoresist.

Napa as a Nanophotonic Ion Source

Highly confined electromagnetic fields play an important role in the interaction of laser radiation with nano structures. Near-field optics show great potential in manipulating light on a sub-micron or even on the molecular scale. Nanophotonics takes advantage of structures that exhibit features commensurate with the wavelength of the radiation. Among others it has been utilized for nanoparticle detection, for the patterning of biomolecules and for creating materials with unique optical properties.

Here, silicon nanopost arrays (NAPA), produced by nanofabrication of silicon surfaces, produce highly uniform nano-scale structures with controlled geometries. NAPA exhibit high absorptance in the 0.2-2.4 μm wavelength range as well as superhydrophobic properties. At sufficiently high laser intensities, the molecules adsorbed on these nanostructures undergo desorption, ionization and eventually exhibit unimolecular decomposition. The resulting ion fragmentation patterns can be used for structure elucidation in mass spectrometry. Importantly, NAPA enable the ultrasensitive MS detection of low mass molecules without external spectral interference since NAPA can directly desorb and ionize analytes subjected to pulsed laser irradiation without the use of matrix molecules.

Here, we describe the production and use of NAPA that harvest light from a laser pulse to produce ions detectable using mass spectrometry and which provide for the identification of sample molecules/adsorbates. The production and use of NAPA made by nanofabrication provides improved ion yields for detecting sample adsorbates during mass spectrometry. Further, these photonic ion sources in combination with the specific geometry of the specially designed nanoposts enable an enhancement and better control of ion production on a micro/nano scale and its direct integration with miniaturized analytical devices.

In a preferred embodiment, there is provided a process for making a silicon nanopost array for detection of a sample through producing ions (photonic ion source) in mass spectrometry, said array adapted to be in cooperative association with a desorption laser having a specific wavelength, said process comprising the steps of: generating by computer aided design (CAD) a nanopost array pattern having a nanopost diameter of about 50 nm to about 800 nm and a periodicity of from about 100 nm to about 1600 nm; writing said pattern using nanolithography onto a silicon wafer made from low resistivity p-type silicon to produce processed areas that are covered with columnar structures having said diameter and said periodicity; developing said processed areas to produce columnar structures comprising a height of about 100 nm to about 2000 nm.

In certain embodiments, the columnar structures are developed by reactive ion etching (RIE).

In certain embodiments of the present invention, there are provided silicon nanopost arrays made by the processes described herein, as well as miniaturized analytical devices such as microfluidic devices, incorporating the silicon nanopost array therein.

In certain embodiments of the present invention, the nanopost arrays are made from silicon substrates. However, it is also contemplated that the arrays may be made from other semiconducting substrate materials, such as germanium, gallium arsenide and the like.

In another embodiment of the present invention, there is provided a laser desorption ionization mass spectrometry system containing i) a silicon nanopost array for holding surface deposited target molecules; ii) a pulsed laser for producing unpolarized or plane polarized radiation impinging on the target molecules for desorption ionization; iii) focusing optics based on lenses, mirrors or a sharpened optical fiber for directing the laser radiation at the nanostructure and the target molecules; and iv) a mass spectrometer for analyzing and detecting the ions that are desorbed from the nanopost array.

In certain embodiments of the present invention, the target molecules for use with the nanopost arrays are selected from the group consisting of pharmaceuticals, dyes, explosives or explosive residues, narcotics, polymers, biomolecules, chemical warfare agents and their signatures, peptides, metabolites, lipids, oligosaccharides, proteins and other biomolecules, synthetic organics, drugs, and toxic chemicals.

In certain other embodiments of the present invention, the nanopost arrays may be used in the detection of microorganisms, such as unicellular eukaryotes, for example, fungi, prokaryotes, for example, bacteria, and viruses, including microorganisms involved in biological warfare. The microorganisms may be applied to the nano device or may be grown directly on the device. For example, microorganisms may be directly grown in a nanopost array, or may be grown in microfluidic growth chambers as part of a nano device. In certain embodiments of the present invention, a nanopost array may be used for the detection of 1000 or fewer, or 100 or fewer or 10 or fewer microorganism cells or viruses. In still other embodiments of the present invention, the nanopost arrays may be used for detecting a single microorganism cell or virus.

In certain embodiments of the present invention, there are also provided methods for the direct chemical analysis of a nanopost-deposited sample by mass spectrometry, including the steps of: subjecting a sample to laser desorption ionization using a photonic ion source; and analyzing the desorbed ions using mass spectrometry; wherein the sample is adsorbed onto the silicon nanopost array, wherein the sample is selected, for example, from the group consisting of pharmaceuticals, dyes, explosives, narcotics, polymers, cells, tissue samples, and biomolecules.

In certain embodiments of the present invention, the laser desorption ionization is performed using a p-polarized laser beam.

The systems of the present invention may be used to provide for enhanced control over ion production and sample molecule fragmentation by adjusting the polarity of the radiation of the desorption laser. In preferred embodiments of the invention, molecule fragmentation and ion production is increased while the plane of polarization of the laser radiation is rotated from s-polarized to p-polarized. Without wishing to be bound by theory, it appears that p-polarized laser light is significantly more efficiently absorbed by the nanopost structures than s-polarized laser light. This appears to result in large post temperature differences, which translate into differences in desorption efficiency and ion yield.

In other embodiments, the present invention encompasses methods for increasing molecular fragmentation and ion production by adjusting the polarization angle of the radiation of the desorption laser. As is described above, in certain embodiments of the invention, the molecular fragmentation and ion production increases as the polarization of the laser radiation is rotated from s-polarized to p-polarized. Once a sample to be analyzed is applied to an array of the present invention, fragmentation and ion production can be increased by rotating the polarization plane of the laser radiation towards p-polarization and decreased by rotating the polarization plane of the laser radiation towards s-polarization. This method allows for control over fragmentation and ionization without the need to attenuate the desorption laser. It also allows for changes to be made in the fragmentation and ion production of a sample within a single system setup.

As a non-limiting example, once a sample is applied to a nanopost array, the array may initially be irradiated with s-polarized light, causing little to no ionization and fragmentation. The plane of the radiation may then be gradually rotated towards p-polarization as is desired by the operator. As the radiation is rotated, the ion production will increase initially producing no or only a few fragments, allowing for the detection of intact molecular ions by the mass spectrometer. For instance, the plane of the radiation may be rotated towards p-polarization in a manner so that the molecular ion peaks, are first detected, followed by increased fragmentation and detection of smaller fragments. Using the methods of the present invention, a broad variety of fragments and ions can be produced and detected from a single system setup.

In another embodiment of the present invention, there is provided a method for direct chemical analysis further comprising the step of controlling ion production by varying laser radiation properties through changes in the angle of incidence and/or the plane of polarization.

In another embodiment of the present invention, there is provided a method of direct chemical analysis further comprising the step of controlling or optimizing ion production by varying the laser radiation/energy coupling properties through changes in the dimensions and periodicity of the nanoposts.

In certain embodiments of the present invention, there are provided nanopost arrays and methods for using them that provide resonant ion production and fragmentation. Certain nanopost arrays of the present invention may show resonance-like behavior leading to enhanced ion production and fragmentation. In certain embodiments, an array with a post diameter of 200 nm and an aspect ratio of 6 shows resonance-like behavior. In other embodiments, an array with a post diameter of 100 nm and an aspect ratio of 10 shows resonance-like behavior. In still other embodiments, an array with a post diameter of 300 nm and an aspect ratio of 4 shows resonance-like behavior. It is also contemplated that other arrays having different post diameters and aspect ratios may show resonance-like behavior, with the general trend that a decrease in post diameter requires an increased aspect ratio to show resonance. Further examples of resonance-like behavior are shown in Example 2 below.

In another embodiment of the present invention, there is provided a method for analysis of a forensic sample, comprising depositing one or more forensic samples onto at least one nanopost array device; directly subjecting the sample without matrix to laser ionization; and detecting the ions using mass spectrometry.

In another embodiment of the present invention, there is provided a method for monitoring the environment, comprising: desorbing one or more environmental samples collected from an environment being tested onto at least one nanopost array device; directly subjecting the environmental sample without matrix to laser ionization; and detecting the ions using mass spectrometry.

In another embodiment of the present invention, there is provided a method of harvesting solar energy, comprising: subjecting one or more nanopost arrays to solar radiation, wherein said nanopost arrays comprise nanoscale columnar structures having one or more electromagnetic radiation-capture coatings, wherein said solar radiation converts said one or more electromagnetic radiation-capture coatings into an electronically converted coating, and withdrawing electronic charge from said electronically converted coating on said nanopost array to supply an electric current.

The systems and methods of the present invention provide many advantages over current systems. In contrast to the conventional soft laser desorption ionization methods, matrix molecules are not needed in the techniques of the present invention. Instead, the nanopost arrays can directly desorb and ionize the analyte upon pulsed laser irradiation.

This simplifies the sample preparation and eliminates spectral interferences created by the matrix molecules.

In addition, unlike laser-induced silicon microcolumn arrays (LISMA), NAPA can be produced with a wide range of geometries enabling a controlled platform for laser desorption ionization MS.

Further, the surface chemistry of NAPA can be altered through standard procedures in microelectronics which creates additional control over the yield and properties of the produced ions.

Still further, the nanofabrication of NAPA lends itself to integration with microfluidic devices.

Various laser sources may be used for sample desorption with the systems and methods of the present invention, including gas lasers such as nitrogen, argon, carbon dioxide and helium-neon lasers, and solid-state lasers, including lasers with solid-state crystals such as yttrium orthovanadate ($YVO_4$), yttrium lithium fluoride (YLF) and yttrium aluminum garnet (YAG) and with dopants such as neodymium, ytterbium, holmium, thulium, and erbium. The NAPA ion production from biomolecules can be manipulated with photonic structures (i.e., photonic ion sources) based on the laser light-nanostructure interaction to improve ion production efficiency and analytical sensitivity.

In certain embodiments, the systems of the present invention are designed using computer aided design. The desorption of samples, including control of the desorption laser, and the analysis of ions produced by the samples may also be controlled by computer. The computing platforms used with the invention perform various functions and operations in accordance with the invention. The computing platform can be, for instance, a personal computer (PC), server or mainframe computer. The computing platform can be a general purpose computer reconfigured by a computer program, or may be specially constructed to implement the features and operations of the system. The computing platform may also be provided with one or more of a wide variety of components or subsystems including, for example, a processor, co-processor, register, data processing devices and subsystems, wired or wireless communication links, input devices, monitors, memory or storage devices such as a database.

All or parts of the system and processes can be stored on or read from computer-readable media. The system can include computer-readable medium having stored thereon machine executable instructions for performing the processes described. Computer readable media may include, for instance, secondary storage devices, such as hard disks, floppy disks, and CD-ROM; a carrier wave received from the Internet; or other forms of computer-readable memory such as read-only memory (ROM) or random-access memory (RAM).

It will be clear to a person of ordinary skill in the art that the above embodiments and Examples below may be altered or that insubstantial changes may be made without departing from the scope of the invention. Accordingly, the scope of the invention should determined by the scope of the following claims and their equitable Equivalents.

EXAMPLES

Example 1: Manufacturing

Nanopost array arrangements were generated by computer aided design (CAD) with the desired post diameter (50 nm to 600 nm) and periodicity (150 nm to 1000 nm) combinations. Mask patterns may be written onto low-resistivity, p-type silicon wafers by nanolithographic production techniques. These may include, without limitation, masked and maskless lithographic processes. Examples of maskless nanolithographic processes include e-beam lithography, focused ion beam, optical, and probe tip/dip-pen.

To achieve ion production using a polarized beam, a plane-polarized beam source is used. A non-limiting example may be a Glan-Taylor calcite polarizer to produce a plane-polarized beam from the laser radiation (for example nitrogen laser at 337 nm wavelength) at polarization angles between s-polarized and p-polarized orientation.

Desorption experiments are conducted according to otherwise standard processes, while maintaining a pulse energy of, for example, approximately 10 µJ.

The orientation of the posts with respect to the beam direction is highly uniform in NAPA since on NAPA substrates the nanopost orientation is perpendicular to the wafer and the mean periodicity of the structure is commensurate with the laser wavelength. Accordingly, the ionization efficiencies of pharmaceuticals and small peptides may be studied as a function of NAPA geometry, focusing on the effect of post diameter, periodicity and post height. And, when the use of a p-polarized beam is added, there is a further increase in ion signal.

The nanofabrication of NAPA greatly enhances its utility as a platform for SLDI-MS based on the strong uniformity of the array and the ability to manipulate the post geometries. The foreseen application of NAPA as an ionization platform includes the detection of a broad range of pharmaceuticals, dyes, explosives or explosive residues, narcotics, polymers, biomolecules, chemical warfare agents and their signatures, peptides, metabolites, lipids, oligosaccharides, proteins and other biomolecules, synthetic organics, drugs, and toxic chemicals with minimal to no interference and ultra-low limits of detection along with structure specific fragmentation capabilities. In addition, NAPA exhibits a unique photonic control of ion production through the manipulation of light on the micro/nano scale leading to the direct integration with microfluidic devices.

Modified or surface derivatized NAPA are included within the scope of the present inventive subject matter. For example, silylated NAPA may be created by oxidizing the wafers in ozone and then treating them with (pentafluorophenyl)-propyldimethylchlorosilane to produce perfluorophenyl (PFP)-derivatized surfaces. These surfaces exhibit enhanced ion yields and reduced fragmentation of the produced ions.

Time-of-flight mass spectrometers may be used for laser desorption ionization experiments. For internal energy measurements, eight benzyl-substituted benzylpyridinium cations with a range of critical energies may be used as thermometer ions (TIs). Survival yields of the molecular ions in unimolecular decomposition may be determined from the mass spectra and correlated to the internal energy of the ions using the RRKM theory. The internal energy of the ions is an important factor that governs ion fragmentation. Ion fragmentation patterns can be used in the structure identification of the related molecule.

NAPA may be produced with column heights ranging from 100 nm to 2000 nm, the diameters of the nanoposts ranging from 50 nm to 800 nm and array periodicities ranging from 100 nm to 1600 nm. Our initial findings revealed that NAPA produced with ~200 nm post diameters and ~1200 nm post heights resulted in the greatest ion intensities (see FIGS. 4A and 4B). Ion yields for substance P as a function of NAPA periodicity, P, for five different post heights (H=400, 800, 1000, 1200 and 1500 nm) revealed that the H=800, 1200 and 1500 nm posts showed a maximum in ion yield at P=~λ=337 nm, i.e., when the periodicity was close to the laser wavelength, λ (see FIG. 5). The arrays made of longer posts, H=1000, 1200 and 1500 nm, also showed a maximum in ion yield at P=~3λ/2=505 nm. In these experiments the post diameters were fixed at D=100 nm.

Figure 4C:
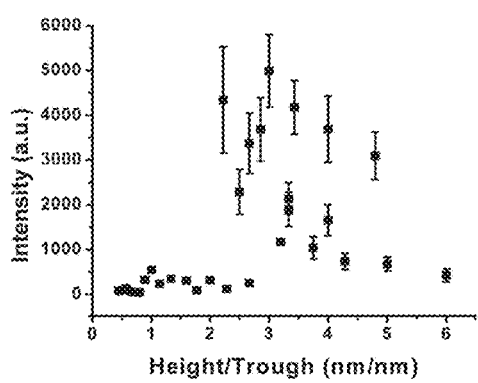
FIG. 4C shows a post height/trough width ratio for 200 nm post diameter.

As a function of the ratio of post heights and trough widths, H/(P−D), there was negligible ion production below a ratio of 2 and a maximum ion yield at a ratio of ~2.5 to 3 (see FIG. 4C). This indicated that the trough dimensions played a role in the ion formation, probably through affecting plume confinement and expansion dynamics.

To gain further insight into the ionization mechanism and how varying the NAPA parameters impacted their ability to couple laser energy into the adsorbates, survival yield experiments were conducted to probe the internal energy of ions. The ions desorbed from NAPA with diameters ranging from 200 nm to 500 nm had steady survival yields at low to medium fluences, and at higher fluences the survival yields increased. In contrast to these findings, NAPA with post diameters of 100 nm exhibited decreasing survival yields as the laser fluence was increased (see FIG. 6). This dramatic disparity indicated that these thinner columns induced a different desorption ionization mechanism. The different desorption ionization regimes were rationalized in terms of the relationship between the laser penetration depth, heat conduction length, and post diameter.

Without being limited to any particular theory, one possible explanation of the improvement seen in p-polarized beams vs. s-polarized beams may be based on the difference in laser radiation-surface coupling for axial vs. transverse excitation of the columns. For example, when the height of the columns is ~2 times the wavelength of the desorption laser, this structure and its electrostatic image in the "ground plane" of the bulk substrate would add to form an efficient antenna for p-polarized, but not for s-polarized, light. It seems likely, therefore, that p-polarized laser light is significantly more efficiently absorbed by the columns than s-polarized. This will result in large post temperature differences, which translate into differences in desorption efficiency and ion yield.

In a simple picture, the absorption efficiency depends on the projection of the electric field from a light wave polarized in the $\varphi_i$ plane onto the microcolumns protruding perpendicular to the substrate, $E_\perp = E_i \sin \vartheta_i \cos \varphi_i$. Thus the part of the laser intensity that is axially absorbed in the columns can be expressed as:

$$I_\perp = I_i \sin^2 \vartheta_i \cos \varphi_i, \quad (1)$$

where the incident light intensity is $I_i = c\varepsilon_0 E_i^2/2$. The extrema of Eq. (1) are consistent with our experimental observations. For right angle illumination ($\vartheta_i = 0°$) with light of any polarization, there is no axial absorption because $I_\perp(\vartheta_i = 0°) = 0$. For a non-zero angle of incidence, e.g., $\varepsilon_i = 45°$, p-polarized beams with $\varphi_i = 180°$ result in maximum energy deposition, whereas for s-polarized radiation, $\varphi_i = 90°$ no axial modes are excited.

In the laser desorption of adsorbates, the aspect ratio of troughs, H/(P−D), where (P−D) is the width of the troughs, impacts a different set of processes. The wide set of geometries achievable for NAPA provide an opportunity to systematically explore these effects. The ability to retain residual solvents and large amounts of adsorbates increases with H/(P−D). Nanoporous desorption substrates in desorption ionization on silicon (DIOS) and in nanostructure-initiator mass spectrometry (NIMS) are extreme examples of high trough aspect ratio structures. As the laser pulse produces a plume from these species, due to confinement effects, the plume density, persistence and chemistry are enhanced for high trough aspect ratios.

The ion production properties of NAPA described above represent an example of nanophotonically modulated ion sources. Due to their structure, energy coupling between the NAPA and the laser radiation is fundamentally different from MALDI, DIOS and NIMS. Thus, they enable the control of ion production by varying the nanostructure geometries. Further control may be obtained by using laser radiation properties other than simple pulse energy, in particular the angle of incidence and the plane of polarization. Accordingly, nanostructure geometries and photonic ion sources promise to enable enhanced control of ion production on a micro/nano scale and direct integration with microfluidic devices.

Experimental Section

Materials:

Low resistivity (0.001-0.005 Ω·cm) p-type mechanical grade, 280±20 μm thick silicon wafers were purchased from University Wafer. Water, xylenes, reagent grade acetone and isopropanol (IPA), substance P, bradykinin, verapamil, and leucine enkephalin were purchased from Sigma-Aldrich.

Nanopost Array Production:

The desired nanopost array patterns were initially generated by a computer-aided design (CAD) program and were used for e-beam lithography. Initial parameters consisted of rectangular packed nanoposts with diameters of 50-600 nm and with trough widths of 100-600 nm.

Mechanical grade p-type silicon wafers (4" diameter) were spin coated by ~2 ml of Zep520A resist at 6000 rpm for 45 seconds and baked at 180° C. for 2 minutes. The e-beam resist coated silicon wafer was placed in a sample holder and inserted into the e-beam lithography instrument (E-Beam Lithography-JEOL JBX-9300 Electron Beam Lithography system at a 100 kV).

To remove the resist exposed to an electron beam, the processed wafers were soaked in xylenes for 30 seconds, washed with isopropanol (IPA), and blow dried in nitrogen gas. Afterwards, the wafer was descummed using a Technics Turbo 810 RIE reactive ion etching (RIE) system at 100 watts for 6 seconds.

100 Å of chromium was deposited onto the wafer at the rate of 1 Å/sec using a thermal evaporator. Excess chromium was removed by sonication in an acetone bath for 2.5 minutes and then the wafer was rinsed in IPA and $H_2O$. Finally, the wafer was blow dried in nitrogen gas.

Various nanopost heights (~200 nm to ~1500 nm) were etched with an Oxford Plasmalab100 RIE/ICP Etcher PECVD system at an etching rate of ~100 nm/min. The resulting NAPA were characterized with an FEI Nova 600 SEM to confirm their dimensions.

Mass Spectrometry Experiments:

A Bruker Daltonics Autoflex II reflectron time-of-flight (TOF) mass spectrometer (MS) was used for initial desorption ionization experiments. NAPA were attached to a MALDI plate with conductive double-sided carbon tape. Solutions of analytes at a concentration of ~1 mg/mL were prepared and deposited onto the NAPA surface at a volume of 0.5 μL and air-dried. Due to the altered electric field and flight length as a result of the addition of the silicon substrate (~300 μm thick) to the target plate, the instrument had to be recalibrated to provide correct mass assignments. Spectra acquired were from 100 laser shot averages in reflectron mode.

Further experiments were conducted on a Kratos Axima III TOF-MS with curved field reflectron. The Kratos instrument used a nitrogen laser focused to ~100 μm diameter spot on the target with adjustable laser fluence. Spectra were acquired from 200 laser shot averages in reflectron mode using 2.5 kV extraction voltage with a 100 ns delay and a 20 kV accelerating voltage.

Survival Yield Experiments:

For laser desorption/ionization experiments 0.5 μL of ~1×10$^{-5}$ M solutions of benzyl substituted benzylpyridinium ions were deposited on NAPA and air-dried. Mass spectra were acquired with the Kratos instrument as described above and the appropriate peaks were integrated in time to calculate the survival yield (SY) of the molecular ion $$SY = \frac{I(M^+)}{I(F^+) + I(M^+)},$$

where M$^+$ and F$^+$ are the abundances of the molecular ion and fragment ion, respectively, as the fluence was varied.

Polarization Experiments:

A 4-ns pulse length and 337 nm wavelength nitrogen laser (VSL-3337ND) was polarized using an uncoated Glan-Taylor calcite polarizer and attenuated with a continuously variable neutral density filter to maintain a consistent pulse energy of ~10 μJ. A high precision rotation mount was used to rotate the plane of polarization from s- to p-polarized. The polarized beam was focused with a fused-silica lens onto the probe tip inside of a home-built TOF-MS creating a laser spot of ~200 μm.

Results and Discussion

FIG. 1 shows the optical (FIGS. 1A and 1B) and SEM images (FIGS. 1C, 1D and 1E) of the produced NAPA along with a sketch (FIG. 1F) indicating the design parameters and the interaction of electromagnetic radiation with the posts.

Figure 2A:
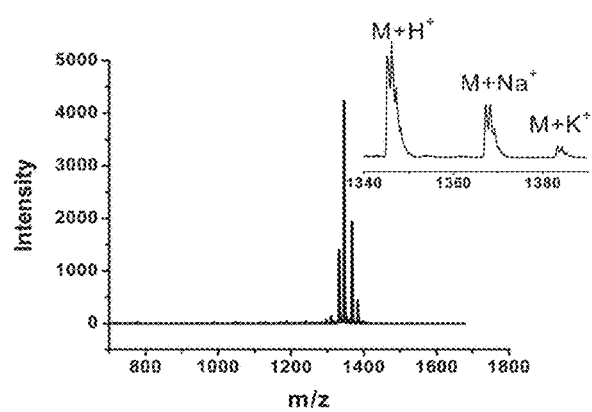
FIG. 2A shows a mass spectra, signal-to-noise ratio (S/N) and mass resolution for substance P analyte from NAPA.
Figure 2B:
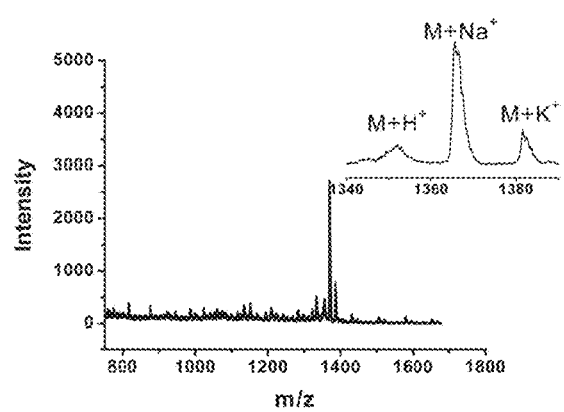
FIG. 2B shows a mass spectra, signal-to-noise ratio and mass resolution for substance P analyte from LISMA platforms.

Figures of merit: Comparison of MALDI, LISMA and NAPA with respect to ion yield, signal-to-noise ratio (S/N), mass resolution, and matrix interference. FIG. 2 compares the typical mass spectra of substance P obtained on a NAPA substrate (FIG. 2A) and on LISMA (FIG. 2B). The NAPA platform provided superior signal-to-noise ratio and mass resolution in the low mass range, compared to the LISMA and especially MALDI (not shown), the spectra from NAPA show dramatically lower chemical background.

The detection limit of verapamil is at least 6 attomoles (see FIG. 3) but the high S/N suggests that smaller amounts could also be detected.

Effect of NAPA Geometries:

The uniformity of NAPA enhances its utility as a platform for SLDI-MS. First, the uniformity of NAPA promotes spot-to-spot reproducibility during experiments, which is not observed in MALDI and less pronounced with LISMA. Second, the manipulation of NAPA geometries through nanofabrication enables parametric studies to explore the mechanism of ionization.

An in depth study was conducted on the effect of nanopost dimensions and periodicity on ionization efficiency. Verapamil and small peptides such as bradykinin, leucine enkephalin, and substance P were used in the experiments. Similar results were found for all analytes. Here, however, we only report the results for verapamil, substance P, and bradykinin. The ion yield of substance P was calculated by taking the sum of the intensities for the molecular ion peak and the corresponding quasi-molecular ion peaks.

Ionization efficiency was studied as a function of NAPA geometry using the following parameters: post height, post diameter, periodicity, trough width, post height/post diameter aspect ratio, post height/trough width aspect ratio, surface area and volume.

Post Height:

FIG. 4A shows that the ion yield of substance P as a function of nanopost height goes through a maximum. The strongest signal for posts of 200 nm diameter and 450 nm periodicity was observed at a height of 1200 nm. It is noted that when the nanoposts are taller than 1200 nm, ion yield drops significantly.

Post Diameter:

FIG. 4B shows that the ion yield of substance P as a function of nanopost diameter goes through a maximum. For 350 nm trough widths, the ion yield was highest at the diameter of 200 nm and decreased at larger diameters.

FIG. 7 shows that 100 nm posts become distorted when exposed to a high fluence desorption laser pulse. At high laser fluences, in addition to a decrease in signal the resolution was greatly reduced and noise increased for 100 and 50 nm posts, most likely due to the deformation of the nanoposts.

NAPA Periodicity:

The effect of periodicity was most clearly revealed for systems with a periodicity-to-diameter ratio larger than three, P/D>3. Ion yields for substance P as a function of NAPA periodicity, P, for five different post heights (H=400, 800, 1000, 1200 and 1500 nm) revealed that the H=800, 1200 and 1500 nm posts showed a maximum in ion yield at P=~λ=337 nm, i.e., when the periodicity was close to the laser wavelength, λ (see FIG. 5). The arrays made of longer posts, H=1000, 1200 and 1500 nm, also showed a maximum in ion yield at P=~3λ/2=505 nm. In these experiments the post diameters were fixed at D=100 nm.

Figure 4D:
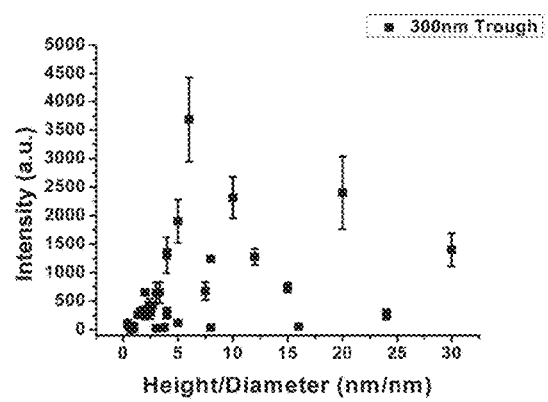
FIG. 4D shows a post height/post diameter ratio for 350 nm trough width.

Other Parameters:

Changes in the trough widths showed the least significant effect on ionization efficiency. However, when the ion yields were followed as the function of the post height to trough width ratios, H/(P−D), a threshold was found, i.e., for ratios less than 2 minimal or no signal was observed followed by a sharp increase in the 2 to 3 region (FIG. 4C). As the ratio further increased (i.e., either the height of the nanoposts increased or the trough width decreased) the ion yields began to decline. A similar relationship was observed for the post aspect ratio, H/D, (see FIG. 4D). In this case, little to no signal was observed below the ratio of 5, followed by a sudden increase that gave way to gradual decrease at higher ratios.

Desorption Ionization Mechanism on NAPA:

A batch of NAPA was produced for further experiments with the following dimensions: 200 nm post diameter, 1000 nm post height and 300 nm trough width. Ion yield as a function of laser polarization was studied on these NAPA. Survival yield as a function of laser fluence was studied on NAPA with H=1000 nm, (P−D)=250 nm and D=50, 100, 200, 300, 400 and 500 nm.

Survival Yield:

The survival yield for the protonated verapamil ion gradually declined with increasing laser fluence. Consequently, structure specific fragmentation could be promoted or suppressed by controlling the fluence of the desorption laser (see FIG. 8).

Survival yields of 4-methyl-benzylpyridinium ions (4M, critical energy=1.6 eV) desorbed from NAPA with 250 nm trough widths, 1000 nm post heights, and various post diameters: 50 nm (■), 100 nm (●), 200 (▲), 300 (▼), 400

(♦), and 500 (◄) were determined. This thermometer ion (TI) desorbed from NAPA with post diameters of 100 nm exhibited decreasing survival yields as the fluence was increased, whereas TIs desorbed from NAPA with larger post diameters had increasing survival yields as the fluence was increased (see FIG. 6). These findings indicated that satisfying the P/D>3 condition resulted in a more straight-forward interpretation of the physical phenomena involved. Among these datasets only the NAPA with 50 nm and 100 nm diameter posts satisfied this condition. Results in the 50 nm dataset were probably influenced by the deformation and melting of these thin posts due to the laser irradiation. The dataset obtained with 100 nm diameter posts exhibits a declining trend with increasing fluence. This indicates an increasing internal energy for the TIs with rising fluence. In case of the larger diameter posts, D=200, 300, 400 and 500 nm, with P/D<3, the onset of other physical processes (e.g., altered and interacting local fields from the posts, altered plume dynamics in the narrow troughs) result in unchanged or increasing survival yields as the fluence is increased.

Polarization Dependent Ion Yields:

Ion yields from NAPA were dramatically affected by the orientation of the plain of polarization for the desorption laser, while MALDI showed no such behavior (see FIG. 9). On the NAPA platform, no signal was detected with s-polarized light and the strongest signal was observed with the p-polarized beam. A possible explanation is based on the dependence of energy coupling between the laser light and the posts on the relative orientation of the electric field vector and the post axis.

Applications of NAPA as an Ionization Platform:

Detection of a range of pharmaceuticals, dyes, explosives or explosive residues, narcotics, polymers, biomolecules, chemical warfare agents and their signatures, peptides, metabolites, lipids, oligosaccharides, proteins and other biomolecules, synthetic organics, drugs, and toxic chemicals with minimal to no interference and ultra-low limits of detection.

The following references are incorporated herein in their entirety as may be necessary to assist a person of ordinary skill in the art to fully understand the claimed invention.

References for Example 1

(1) Tanaka, K. W., H.; Ido, Y.; Akita, S.; Yoshida, Y.; Yoshida, T. *Rapid Commun. Mass Spectrom.* 1988, 2, 151-153.
(2) McLean, J. A.; Stumpo, K. A.; Russell, D. H. *Journal of the American Chemical Society* 2005, 127, 5304-5305.
(3) Schaaff, T. G. *Analytical Chemistry* 2004, 76, 6187-6196.
(4) Castellana, E. T.; Russell, D. H. *Nano Letters* 2007, 7, 3023-3025.
(5) Go, E. P.; Apon, J. V.; Luo, G.; Saghatelian, A.; Daniels, R. H.; Sahi, V.; Dubrow, R.; Cravatt, B. F.; Vertes, A.; Siuzdak, G. *Analytical Chemistry* 2005, 77, 1641-1646.
(6) Luo, G. H.; Chen, Y.; Daniels, H.; Dubrow, R.; Vertes, A. *Journal of Physical Chemistry B* 2006, 110, 13381-13386.
(7) Wei, J.; Buriak, J. M.; Siuzdak, G. *Nature* 1999, 399, 243-246.
(8) Luo, G. H.; Chen, Y.; Siuzdak, G.; Vertes, A. *Journal of Physical Chemistry B* 2005, 109, 24450-24456.
(9) Trauger, S. A.; Go, E. P.; Shen, Z. X.; Apon, J. V.; Compton, B. J.; Bouvier, E. S. P.; Finn, M. G.; Siuzdak, G. *Analytical Chemistry* 2004, 76, 4484-4489.
(10) Nordstrom, A.; Apon, J. V.; Uritboonthal, W.; Go, E. P.; Siuzdak, G. *Analytical Chemistry* 2006, 78, 272-278.
(11) Go, E. P.; Shen, Z. X.; Harris, K.; Siuzdak, G. *Analytical Chemistry* 2003, 75, 5475-5479.
(12) Northen, T. R.; Yanes, O.; Northen, M. T.; Marrinucci, D.; Uritboonthai, W.; Apon, J.; Golledge, S. L.; Nordstrom, A.; Siuzdak, G. *Nature* 2007, 449, 1033-U1033.
(13) Chen, Y.; Vertes, A. *Analytical Chemistry* 2006, 78, 5835-5844.
(14) Gorecka-Drzazga, A.; Dziuban, J.; Drzazga, W.; Kraj, A.; Silberring, J. *Journal of Vacuum Science & Technology B* 2005, 23, 819-823.
(15) Crouch, C. H.; Carey, J. E.; Warrender, J. M.; Aziz, M. J.; Mazur, E.; Genin, F. Y. *Applied Physics Letters* 2004, 84, 1850-1852.
(16) Her, T. H.; Finlay, R. J.; Wu, C.; Deliwala, S.; Mazur, E. *Applied Physics Letters* 1998, 73, 1673-1675.
(17) Her, T. H.; Finlay, R. J.; Wu, C.; Mazur, E. *Applied Physics a-Materials Science & Processing* 2000, 70, 383-385.
(18) Pedraza, A. J.; Fowlkes, J. D.; Guan, Y. F. *Applied Physics a-Materials Science & Processing* 2003, 77, 277-284.
(19) Pedraza, A. J.; Fowlkes, J. D.; Lowndes, D. H. *Applied Physics Letters* 1999, 74, 2322-2324.
(20) Pedraza, A. J.; Fowlkes, J. D.; Lowndes, D. H. *Applied Physics Letters* 2000, 77, 3018-3020.
(21) Kuo, T. F.; Xu, J. J. *Vac. Sci. Technol. B* 2006, 24, 1925-1933.
(22) Arney, S.; Kroupenkine, T. N.; Lyons, A. M.; Mandich, M. L.; Schabel, M. J.; Taylor, J. A. Dynamically controllable biological/chemical detectors having nanostructured surfaces, 2006, U.S. Pat. No. 7,048,889.
(23) Walker, Bennett N.; Razunguzwa, T.; Powell, M.; Knochenmuss, R.; Vertes, A. *Angewandte Chemie International Edition* 2009, 48, 1669-1672.

Example 2: Tailored Silicon Nanopost Arrays for Resonant Nanophotonic Ion Production Quasiperiodic columnar silicon nanostructures offer low reflectivity in a wavelength range spanning from 200 nm through mid-IR[1] to the terahertz region[2]. Examples include laser-induced silicon microcolumn arrays (LISMA)[3] produced by femtosecond laser surface structuring[4] and silicon nanotip (SiNT) arrays fabricated by plasma etching[2]. These high aspect ratio structures offer sub-band gap light absorption with a corresponding photocurrent, broadband anti-reflection properties, efficient electron emission[5] and superhydrophobic behavior[6].

Nanoscopic protrusions on silicon surfaces are known to result in the local enhancement of electromagnetic radiation that, for a 10:1 aspect ratio column, can reach an intensity gain close to 200 in the near field[7]. Metal nanostructures can exhibit additional enhancements through surface plasmon resonances and operate as optical antennas[8-10]. These structures demonstrate resonant energy absorption[11] that is sensitive to polarization[12] and antenna length[9], and their near-field response can be tuned through altering the geometry[13]. Near-field radiation induced fluorescence has been demonstrated in biological membranes[14] and single molecules[15] opening the way for the microscopy and spectroscopy of sub-wavelength domains. At higher laser fluences materials brought to the proximity of these enhanced fields can undergo ablation[16,17] that can include the nanoscopic structure producing the enhancement itself[18]. In particular, gold nanoparticle ablation induced by the near field sets in between 9 and 12 mJ/cm$^2$, whereas melting only commences at 15 mJ/cm$^2$ [18].

Nanostructures that have dimensions commensurate with the wavelength of the electromagnetic radiation exhibit near-field effects[19,20] and, as optical antennas, can couple laser radiation to the local environment[21]. We have recently discovered that increasing the laser intensity on LISMA structures covered with biomolecules results in adsorbate ion production[3] and this process exhibits nanophotonic behavior[22]. Features of ion production from LISMA include polarization and incidence angle dependent ion yields, and the ability to adjust the degree of ion fragmentation through the laser fluence[3,22]. As the laser intensity is increased, structure specific fragment ions resulting from both low energy and high-energy processes are observed.[23] These results indicate that surface collisions, in-plume reactions, and the enhancement of the electromagnetic field near the microcolumns may all play a role in ion production from these sources. Due to the narrow range of array geometries accessible through laser surface structuring[24], there are limited possibilities for tuning the interaction between the LISMA structure and the laser radiation.

Silicon nanopost arrays (NAPA) are similar to LISMA in their chemical composition and overall morphology. Due to the nanofabrication used in their production, however, we have a greater control over the relevant dimensions. The schematic of a NAPA, along with the relevant dimensions and the electric field of the incident laser beam is shown in FIG. 10A.

In this work, we explore laser desorption ionization from tailored NAPA produced by fabrication in a wide range of post diameters, heights and periodicities. Ion production from NAPA structures upon exposure to laser radiation was explored for a range of dimensions and laser fluences. Our results show that selecting certain post aspect ratios give rise to a resonance in ion production.

Experimental Section

Nanopost Array Fabrication.

Low resistivity (0.001-0.005 Ω·cm) p-type silicon wafers were spin coated by ZEP520A resist at 6000 rpm for 45 seconds and baked at 180° C. for 2 minutes. A variety of rectangular packed patterns for cylindrical NAPA were produced by e-beam lithography (JEOL JBX-9300). Nanopost diameters and periodicities were systematically varied from 50 to 600 nm, and from 200 to 1200 nm, respectively. To remove the exposed resist, wafers were soaked in xylenes for 30 seconds, rinsed with isopropanol, and blow dried with nitrogen gas. The wafer was descummed in an oxygen plasma at 100 watts for 6 seconds using a Technics reactive ion etching system. A 10-nm chromium layer was deposited onto the wafer at a rate of 0.1 nm/sec using an electron beam evaporator. Sonication of the wafer in an acetone bath for 2.5 minutes dissolved the unexposed resist and removed the chromium layer from those areas. Various nanopost heights (~200 nm to ~1500 nm) were produced at a rate of ~100 nm/min by an Oxford PlasmaLab100 reactive ion etching system using a combination of $C_4F_8$ and $SF_6$ gases. The integrity and the dimensions of the resulting NAPA were inspected using a scanning electron microscope (FEI Nova Nanolab 600 DualBeam™) system (see FIG. 10B).

Mass Spectrometry. Following the nanofabrication process, the laser desorption ionization properties of the NAPA were confirmed using a Bruker Daltonics Autoflex II reflectron time-of-flight mass spectrometer (TOF-MS). Adsorbate solutions of substance P, bradykinin, leucine enkephalin, angiotensin I, GFL and verapamil were prepared at a concentration of ~1 mg/mL in 50% methanol. A 0.5 μL aliquot of a solution was deposited onto the NAPA surface and air dried. Averaged mass spectra were acquired from 100 laser shots in reflectron mode. More detailed experiments, aimed at the fluence dependence of the ion yield and the fragmentation behavior, were conducted on a Kratos Axima III TOF-MS with a curved field reflectron. The Kratos instrument used a nitrogen laser focused to ~100 μm diameter spot with adjustable laser fluence on the NAPA target. Averaged spectra were acquired from 200 laser shots in reflectron mode using a 2.5 kV extraction voltage with a 100 ns delay and a 20 kV accelerating voltage.

Polarized Laser Desorption Ionization.

Radiation from an LSI nitrogen laser (VSL-337ND) was polarized using an uncoated Glan-Taylor calcite polarizer in a rotation mount. The 4 ns laser pulses were attenuated with a continuously variable neutral density filter to maintain a pulse energy of ~10 μJ while the plane of polarization was rotated between s- and p-polarized. The polarized beam was focused with a fused silica lens to a ~200 μm spot on the NAPA structures in the source region of a home-built time-of-flight mass spectrometer.

Energy Deposition Modeling.

To model the energy deposition and redistribution in the nanoposts, a three-dimensional finite difference scheme was implemented with an adaptive mesh. With the help of the FlexPDE 6.06 (PDE Solutions, Inc.) package, Equation 2 was solved for a single post with insulating boundary conditions, except for the base of the post, where heat conduction to the silicon wafer was allowed. The laser pulse was represented by a uniform intensity distribution of $6 \times 10^6$ $W/cm^2$ along the post. The thermal conductivity and specific heat of silicon were treated as temperature dependent parameters.

Results and Discussion

NAPA Production.

Figure 1A:
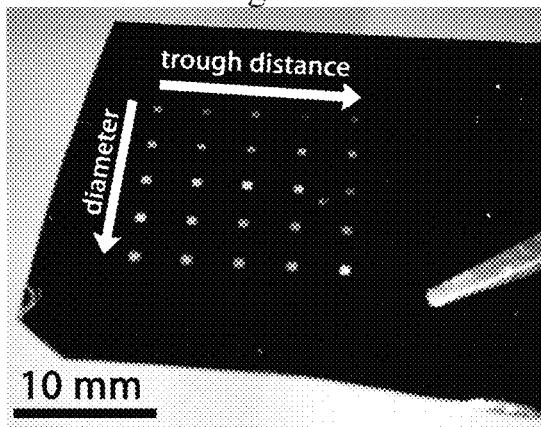
FIG. 1A shows an optical image of a silicon wafer with a 5×6 array of NAPA of varying post diameters and trough widths.
Figure 1B:
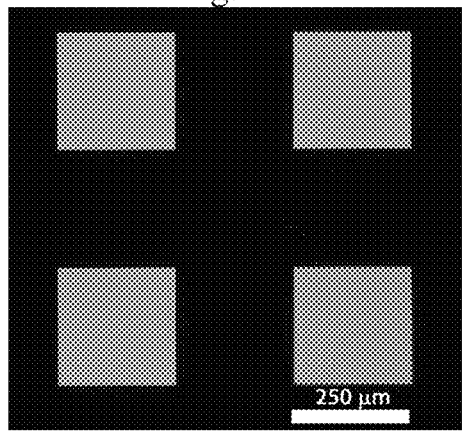
FIG. 1B shows a microscope image of NAPA with 400 nm post diameter and 350 nm trough width shows unique color.
Figure 1C:
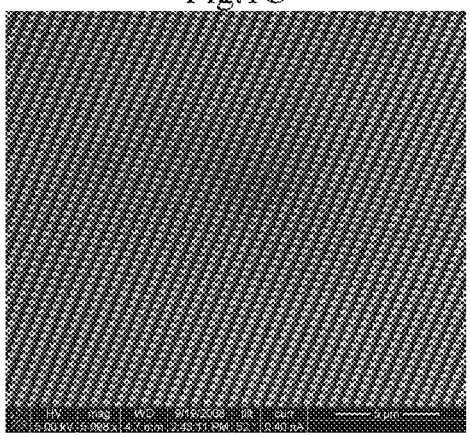
FIG. 1C shows a scanning electron microscope (SEM) image at low magnification shows uniform post diameters and periodicity in NAPA.
Figure 1D:
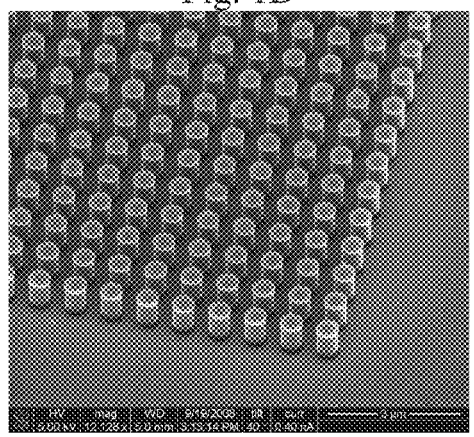
FIG. 1D shows a SEM image shows the well defined boundaries at the corner of NAPA.
Figure 1E:
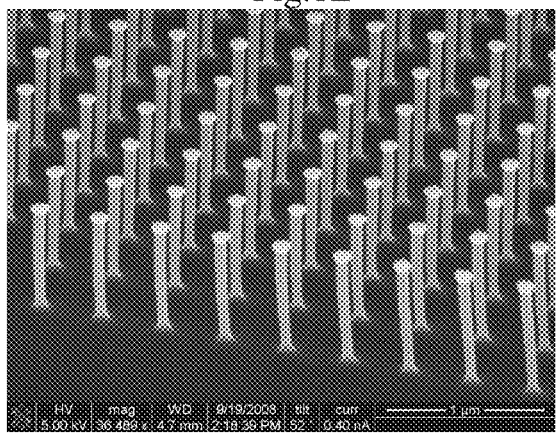
FIG. 1E shows a SEM image at high magnification shows NAPA with 100 nm post diameter and 450 nm trough width.
Figure 1F:
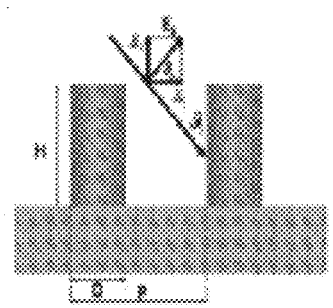
FIG. 1F shows a sketch of NAPA with post height, H, diameter, D, and periodicity, P. The electric field vector of the incident laser beam, $E_i$, its orthogonal projections and relationship to the posts are also depicted.

The cylindrical post diameters, D, heights, H, and periods, P, are varied in the D=50-600 nm, H=200-1,500 nm, and P=200-1,200 nm ranges, respectively. The arrays are established on a rectangular grid of 500 μm on each side. Thus the array sizes are 2,500×2,500=6,250,000 posts for P=200 nm, and 416×416=173,056 posts for P=1200 nm. FIG. 1B shows the scanning electron microscope (SEM) image of a segment of the NAPA produced by anisotropic reactive ion etching (RIE) which achieves uniform post heights with vertical walls and minimum tapering. The 10 nm thick chromium top on the posts is necessary for the RIE process that produces posts with aspect ratios up to H/D=15. To rule out the possible effect of these chromium caps on the nanophotonic behavior, we refer to similar findings in the case of LISMA structures. Those systems do not have chromium caps, yet they exhibit many similar nanophotonic properties, such as the polarization dependent ion yields discussed below.

Laser Desorption Ionization Mass Spectra from NAPA.

Small organics and biomolecules, deposited on the NAPA structures, are efficiently desorbed and ionized by 337 nm nitrogen laser radiation of ~20 $mJ/cm^2$ and above. FIG. 2A depicts the high mass region of the low fluence mass spectrum of the neuropeptide substance P (RPKPQQFF-GLM). The peptide sequences are described by one letter code and the fragmentation nomenclature follows the conventions introduced by Biemann[25]. Protonated molecules are produced with high abundance accompanied by low amounts of alkalinated products and a fragment corresponding to m/z 14 loss. In the low mass region (m/z<560), backbone cleavage ($a_2$, $b_2$), internal fragments (PK-28/KP-28, QF, KPQ-28) and immonium ions (R-87 or P-17, K/Q, K/Q-28, M-28, R-45, F-28, K/Q-45) are prevalent. Other small peptides (bradykinin (RPPGFSPFR), leucine enkephalin (YGGFL), angiotensin I (DRVYIHPFHL), GFL, etc.) give similar results.

Small organics composed of preformed ions (organic salts), like verapamil hydrochloride, produce very clean spectra (not shown) dominated by the protonated molecule, with negligible fragmentation corresponding to the loss of the 3,4-dimethoxyphenylmethyl moiety. Preformed ions exist as charged entities already in the solid phase or as an adsorbate. Thus they do not require an ionization step and can be used to probe the desorption process separately. The desorption of verapamil from the NAPA structure is found to be very efficient resulting in an ultralow detection limit of 6 attomoles.

The reusability of NAPA was investigated by taking mass spectra of various peptides repeatedly from the same substrate and sonicating it in methanol and water baths between the experiments. Our results showed minimal cross contamination between runs and no nanopost damage was observed after sonication. The minor cross contamination is likely due to the ultra low limit of detection, pointing to the importance of thorough cleaning between experiments. Furthermore, storage of the NAPA structures for over 1.5 years did not impact the performance of these structures. These results indicate the potential for reusability for these structures and stability in the ambient environment.

Resonant Ion Production and Fragmentation.

To explore the impact of NAPA geometries on peptide ion production, the yields of quasimolecular ions are followed for a variety of nanofabricated structures. Of the three main parameters, D, H and P, the post heights have the strongest influence on the ion yields. FIG. 2B shows the yields of substance P ions as a function of the post aspect ratio, H/D, for different post diameters. Compared to the H/D=1 case, the large diameter posts, D=500 and 400 nm, have modest ion yield maxima at the low aspect ratios of 2.4 and 3, respectively, that show a factor of 7 increase. As the posts become thinner, D=300, 200 and 100 nm, the maxima shift to higher aspect ratios, H/D=4, 6 and 10, respectively, and the ion yields show more dramatic gains. The largest gain, a factor of 55 compared to the H/D=1 case, is observed for D=200 nm at an aspect ratio of six. In terms of post height, the D=500, 400, 300 and 200 posts show maximum ion yields at H=1,200 nm and the D=100 nm post is most efficient at H=1,000 nm. This corresponds to H/λ≈3.0 to 3.6 and an optimum gain of 55.

This resonance-like behavior is analogous to the aspect ratio-dependent gains in the near-field intensity observed for spheroidal silicon protrusions through fluorescence[7,26]. Studying the effect of probe length on field enhancement around an apertureless near-field probe, Bohn and coworkers have found that for a tip radius of curvature $R_c$=10 nm the intensity enhancement of $\kappa^2$≈225 is the highest at a/$R_c$≈12, where a is the semimajor axis length of the spheroid. They attributed the drop-off of the enhancement at higher aspect ratios to the emergence of internal resonances in the probe. For the protrusion with $R_c$=5 nm the enhancement factor continues to grow up to $\kappa^2$≈250 at a/$R_c$≈20, the highest studied aspect ratio. The general trend in this data is similar to our ion yield observations. Slender posts in both cases produce strong enhancement in the signal at aspect ratios that shift to higher values for smaller diameters. Despite the similarities, the interactions of the posts with the laser radiation are significantly different in the two studies. This is directly manifested in the corresponding skin depth, δ, values. While the silicon in the fluorescence study has a skin depth of ~1100 nm, i.e., their near-field probe is practically transparent, in our work, δ≈84 nm resulting in strong absorption of the incident light in the posts. Further differences arise from the interactions between the posts in our large arrays.

To uncover the effect of periodicity on the ion yields, arrays of D=200 nm posts and different periods, P=450, 500, 550 and 600 nm, are compared as a function of the aspect ratio. The results for substance P are summarized in FIG. 11C. All four arrays produce maximum ion yields at H/D≈6, but the amplitudes of the gains, 18 and 30 for P=450 and 600 nm, respectively, are somewhat different. This modest dependence on the period indicates that most of the enhancement is caused by near-field effects around a post that are only weakly influenced by the presence of other posts in the array.

The two most significant factors that influence the desorption and ionization of adsorbates are the near-field enhancement of the laser intensity and the heating of the posts by the radiation. The electric field, E, at a distance r from the surface of the post can be approximated as[7] $E=-\kappa|E_p|(D/(D+2r))^3 r$ and $E_p=E_i \sin\theta \cos\phi$, where $E_p$ is the component of the laser electric field vector that is parallel with the posts, θ is the angle of incidence, φ is the polarization angle, and r is a unit vector pointing away from the post. Thus, the enhanced laser intensity at the top of the post decays as, $$I(r): I(r) = -\kappa^2 I_i \sin^2\theta \cos^2\phi \left(\frac{D}{D+2r}\right)^6, \quad (1)$$

where $I_i$ is the incident laser intensity. Therefore, the enhanced intensity depends on the angle of incidence and the polarization angle, and decays rapidly with the distance from the surface.

Adsorbates close to the surface experience strong electric fields and radiation intensities that, depending on the aspect ratio of the posts, can be up to 200 times higher than the incident laser intensity. These conditions can promote ionization and induce fragmentation through a yet unknown mechanism. Table 1 summarizes the fragment ions produced by a nitrogen laser pulse on a typical NAPA from model peptides GFL and substance P. In addition to some of the a, b and y-series ions commonly observed in high energy collision activated dissociation (CAD)[27] and in surface induced dissociation (SID)[28], the decomposition products observed from NAPA include internal fragments and immonium ions. In place of the commonly observed ammonia loss from the protonated molecule at low energies, the loss of 14 Da is detected. Based on the size distribution and the nature of the fragments it seems that low energy and high energy decomposition channels are operational simultaneously. Currently only nanophotonic ionization techniques, LISMA and NAPA, produce peptide molecular ions and their structure specific fragments without additional ion activation.

TABLE 1

Fragmentation of small peptides in laser desorption ionization from NAPA substrates (D = 200 nm, H = 1000 nm and P = 500 nm for substance P and D = 200 nm, H = 800 nm and P = 500 nm for GFL).

| Peptides | Quasi-molecular ions | 14 loss | Fragment ions[a] | | | | | Internal fragments | Immonium ions[b] |
| --- | --- | --- | --- | --- | --- | --- | --- | --- | --- |
| | | | a ions | b ions | c ions | y ions | Y ions | | |
| GFL | M + H, M + Na, M + K | M + H-14 | $a_2$ | $b_2$ | $c_2$ | $y_1, y_2$ | Y1 | | F-28 |
| Substance P | M + H, M + Na, M + K | M + H-14 | $a_2$, $a_2$-$NH_3$ | $b_2$ | $c_2$ | | | PKPQQ-28, PQQ, KPQ-28 | R-87 or P-17, K/Q, K/Q-28, M-28, R-45, F-28, K/Q-45 |

[a]The peptide fragmentation nomenclature follows the conventions introduced by Biemann[25].
[b]Immonium ions undergo consecutive losses of 17, 12, 29, etc. This notation starts from the intact immonium ion of a residue and marks the losses in nominal mass units Polarization Dependent Ion Yields.

It has been shown that polarization and incidence angle dependent strong optical fields can be generated between a sharp metal tip and a surface[29]. Even without plasmon resonance, strong field enhancement is observed for p-polarized light, whereas s-polarized beams produce no enhancement. Polarization dependent ion production has also been demonstrated for LISMA substrates[22]. Here we show that laser desorption ionization from the NAPA structures at constant fluence exhibits strong polarization angle dependence. FIG. 12 summarizes the results for the ion yields of verapamil and bradykinin as a function of $\phi$ between 60° and 220°. Verapamil follows a close to $\cos^2\phi$ behavior, with strong ion production for p-polarized light and close to zero ion yields for s-polarized radiation. Although the general trend is similar, bradykinin and angiotensin I (not shown) ion yields approximate a cusp in the p-polarized region and drop to zero in a wide range (from 60° to 130°) around the s-polarized orientation. Since verapamil exists in ionic form already as an adsorbate, ion production only requires a desorption step, whereas for the peptides an ionization step, e.g., proton transfer, is also required. This additional ionization step needed for peptides might be responsible for the differences in the shapes of the ion yield curves in FIG. 12.

Modeling of Energy Deposition.

Figure 3:
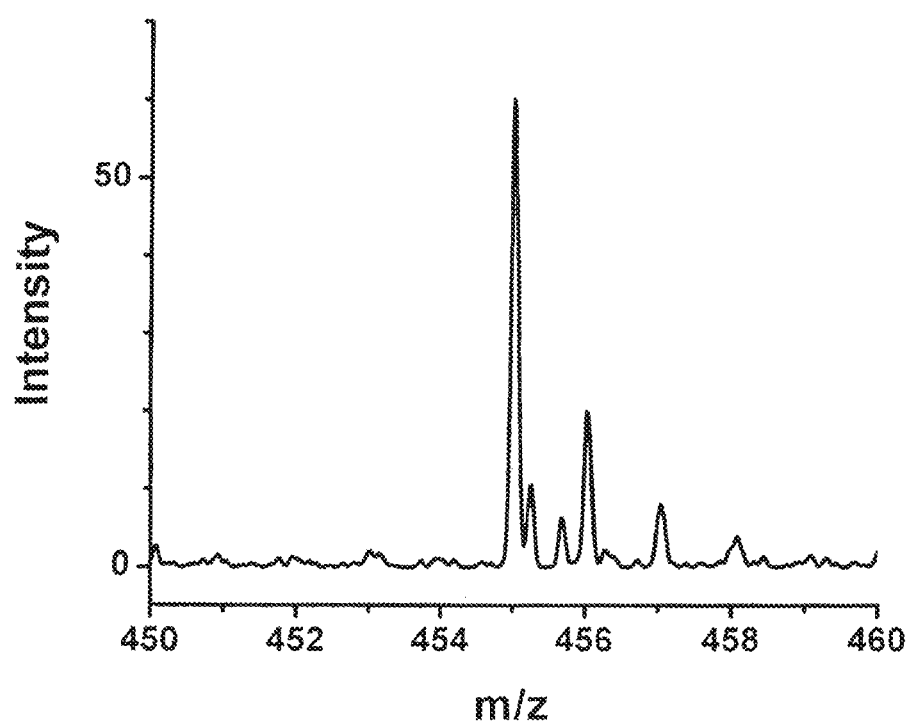
FIG. 3 shows a strong protonated molecular signal is observed in the mass spectrum of 6 attomoles of verapamil indicating an ultralow limit of detection.

Ion production from adsorbates on NAPA can be rationalized by the onset of several processes: energy concentration and deposition induced by the interaction of the laser radiation with the NAPA, energy redistribution in the quasi one-dimensional posts, and the desorption, ionization and activation of the adsorbed species. Energy deposition into the nanoposts is governed by the power dissipation in their volume, $dP/dV = J \cdot E_i$, where $J = \sigma \cdot E_p$ is the current induced by the electric field in the posts and $\sigma$ is their conductivity. The penetration of the electric field into the posts, therefore, the region with significant current and dissipation is determined by the skin depth, which for our low resistivity silicon at 337 nm wavelength is 84 nm. The surface current, $J_s$, decays with the distance, d, from the surface as $J = J_s \exp(-d/\delta)$. Thus to follow the energy redistribution the heat conduction equation has to be solved for a penetrating volume source. For posts thinner than the phonon mean free path, which for silicon nanoposts at 300 K is ~800 nm[30], the Fourier heat conduction equation is replaced by the ballistic-diffusive heat transport equation. The difference between the two approaches is most pronounced at short time scales[31,32], so for the calculation of the post surface temperatures at the end of the laser pulse we use the former.

$$\frac{\partial T}{\partial t} = \nabla\left(\frac{K(T)V}{C_p}\nabla T\right) + (1-R)\frac{V}{\delta C_p}I_i\sin^2\theta\cos^2\varphi\exp(-d/\delta), \quad (2)$$

where $K(T)$, $C_p$, R and V are the temperature dependent thermal conductivity, heat capacity, reflectance and molar volume, respectively. The FlexPDE finite element package is used with an adaptive mesh to solve Eq. (2) for the nanopost geometry. Surface temperatures, $T_{surf}$, are calculated on the irradiated side of the nanopost at the end of the laser pulse. For D=300 nm posts, the results indicate that the surface temperature is a strong function of the polarization angle. At 24 mJ/cm², temperatures for p-polarized light reach 1,228 K, whereas no heating is predicted for s-polarized radiation. FIG. 3 indicates that the ion production is a threshold process, with an earlier onset for verapamil that requires only a desorption step compared to bradykinin that relies on an additional ionization step for ion production. Compared to verapamil, the relative ion yield values at the maximum are 1.4× lower for bradykinin and 1.6× lower for angiotensin I.

Modeling based on equation (2) also demonstrates that NAPA with thinner posts reach increasingly higher surface temperatures. This effect sets in as the post diameters become smaller than the heat diffusion length, l, in silicon. Due to the temperature dependence of K and $C_p$, for a τ=5 ns laser pulse $l = \sqrt{K(T)V\tau/C_p}$ drops from 730 nm at 300 K to 230 nm at 1,600 K. FIG. 4 demonstrates that based on equation (2), indeed, at a laser fluence of 30 mJ/cm² the surface temperature of 100-nm diameter posts temporarily exceeds the melting point. SEM images of NAPA, after exposure to laser radiation, confirm this prediction (see insets in FIG. 13).

CONCLUSIONS

Nanophotonic ion production was first demonstrated on LISMA substrates[22]. Strong fields enhancements near the nanoposts are thought to contribute to ion formation. Due to the limitations of the laser surface processing involved in their production, those structures are restricted to diameters of 300 nm and above, and maximum aspect ratios of two. Nanofabrication of NAPA can produce structures with three times smaller diameters and with aspect ratios up to H/D=15. These higher aspect ratio structures have significantly increased local fields that can promote ionization. Laser desorption ionization experiments show resonant ion production from these slender posts with a 55-fold enhancement.

In addition, a dramatic increase of the ion yield is observed as the angle of polarization transitions from the s- to p-polarized, indicating a similarity to antenna arrays. The strong polarization dependence of the ion yields from NAPA enables the rapid modulation and switching of ion production.

The diameter of slender posts is close to the heat diffusion length. Therefore, these posts reach higher surface temperatures and can more efficiently transfer energy to the adsorbate. As a result, NAPA-based ion sources offer adjustable fragmentation not available for ion sources currently used in the structure elucidation of peptides and proteins. The traditional techniques rely on CAD or other ion activation techniques to produce structure specific fragments.

Further development and understanding of these nanophotonic ion sources can lead to a highly efficient ion source capable of controlling the degree of fragmentation for various biomolecules. The size, material and fabrication of NAPA structures make them amenable to eventual integration with microfluidic devices and micromachined mass spectrometers.

References for Example 2

(1) Crouch, C. H.; Carey, J. E.; Warrender, J. M.; Aziz, M. J.; Mazur, E.; Genin, F. Y. *Applied Physics Letters* 2004, 84, 1850.
(2) Huang, Y. F.; Chattopadhyay, S.; Jen, Y. J.; Peng, C. Y.; Liu, T. A.; Hsu, Y. K.; Pan, C. L.; Lo, H. C.; Hsu, C. H.; Chang, Y. H.; Lee, C. S.; Chen, K. H.; Chen, L. C. *Nature Nanotechnology* 2007, 2, 770.
(3) Chen, Y.; Vertes, A. *Analytical Chemistry* 2006, 78, 5835.
(4) Her, T. H.; Finlay, R. J.; Wu, C.; Deliwala, S.; Mazur, E. *Applied Physics Letters* 1998, 73, 1673.
(5) Zorba, V.; Tzanetakis, P.; Fotakis, C.; Spanakis, E.; Stratakis, E.; Papazoglou, D. G.; Zergioti, I. *Applied Physics Letters* 2006, 88, 081103.
(6) Zorba, V.; Persano, L.; Pisignano, D.; Athanassiou, A.; Stratakis, E.; Cingolani, R.; Tzanetakis, P.; Fotakis, C. *Nanotechnology* 2006, 17, 3234.
(7) Hamann, H. F.; Gallagher, A.; Nesbitt, D. J. *Applied Physics Letters* 2000, 76, 1953.
(8) Farahani, J. N.; Pohl, D. W.; Eisler, H. J.; Hecht, B. *Physical Review Letters* 2005, 95, 017402.
(9) Muhlschlegel, P.; Eisler, H. J.; Martin, O. J. F.; Hecht, B.; Pohl, D. W. *Science* 2005, 308, 1607.
(10) Cubukcu, E.; Kort, E. A.; Crozier, K. B.; Capasso, F. *Applied Physics Letters* 2006, 89, 3.
(11) Crozier, K. B.; Sundaramurthy, A.; Kino, G. S.; Quate, C. F. *Journal of Applied Physics* 2003, 94, 4632.
(12) Fischer, H.; Martin, O. J. F. *Journal of the European Optical Society-Rapid Publications* 2008, 3, 08018.
(13) Merlein, J.; Kahl, M.; Zuschlag, A.; Sell, A.; Halm, A.; Boneberg, J.; Leiderer, P.; Leitenstorfer, A.; Bratschitsch, R. *Nature Photonics* 2008, 2, 230.
(14) Sanchez, E. J.; Novotny, L.; Xie, X. S. *Physical Review Letters* 1999, 82, 4014.
(15) Anger, P.; Bharadwaj, P.; Novotny, L. *Physical Review Letters* 2006, 96, 113002.
(16) Stockle, R.; Setz, P.; Deckert, V.; Lippert, T.; Wokaun, A.; Zenobi, R. *Analytical Chemistry* 2001, 73, 1399.
(17) Hwang, D. J.; Chimmalgi, A.; Grigoropoulos, C. P. *Journal of Applied Physics* 2006, 99, 044905.
(18) Plech, A.; Kotaidis, V.; Lorenc, M.; Boneberg, J. *Nature Physics* 2006, 2, 44.
(19) Girard, C. *Reports on Progress in Physics* 2005, 68, 1883.
(20) Coyle, S.; Netti, M. C.; Baumberg, J. J.; Ghanem, M. A.; Birkin, P. R.; Bartlett, P. N.; Whittaker, D. M. *Physical Review Letters* 2001, 87, 176801.
(21) Taminiau, T. H.; Stefani, F. D.; Segerink, F. B.; Van Hulst, N. F. *Nature Photonics* 2008, 2, 234.
(22) Walker, B. N.; Razunguzwa, T.; Powell, M.; Knochenmuss, R.; Vertes, A. *Angewandte Chemie-International Edition* 2009, 48, 1669.
(23) Stolee, J. A.; Chen, Y.; Vertes, A. *Journal of Physical Chemistry C* 2009, Web released, DOI: 10.1021/jp906834z.
(24) Akhmanov, S. A.; Emelyanov, V. I.; Koroteyev, N. I.; Seminogov, V. N. *Uspekhi Fizicheskikh Nauk* 1985, 147, 675.
(25) Biemann, K. *Biomedical and Environmental Mass Spectrometry* 1988, 16, 99.
(26) Bohn, J. L.; Nesbitt, D. J.; Gallagher, A. *Journal of the Optical Society of America A* 2001, 18, 2998.
(27) Vachet, R. W.; Winders, A. D.; Glish, G. L. *Analytical Chemistry* 1996, 68, 522.
(28) Nair, H.; Somogyi, A.; Wysocki, V. H. *Journal of Mass Spectrometry* 1996, 31, 1141.
(29) Martin, O. J. F.; Girard, C. *Applied Physics Letters* 1997, 70, 705.
(30) Luo, G. H.; Chen, Y.; Daniels, H.; Dubrow, R.; Vertes, A. *Journal of Physical Chemistry B* 2006, 110, 13381.
(31) Chen, G. *Physical Review Letters* 2001, 86, 2297.
(32) Joshi, A. A.; Majumdar, A. *Journal of Applied Physics* 1993, 74, 31.

What is claimed is:

1. A method for the direct chemical analysis of a nanopost-deposited sample by mass spectrometry, the method comprising
   (a) depositing the sample onto a nanopost array mask pattern arrangement having a nanopost diameter of about 50 nm to about 800 nm and a periodicity of from about 100 nm to about 1600 nm, wherein said mask pattern is written onto a substrate comprising silicon or semiconductor material, and wherein said substrate comprises processed areas that are covered with columnar structures having said diameter and said periodicity and a height of about 100 nm to about 2000 nm;
   (b) subjecting the sample to laser desorption ionization using a photonic ion source; and
   (c) analyzing the produced ions using mass spectrometry.

2. The method of claim 1, further comprising the step of controlling ion production and molecular fragmentation by varying laser radiation properties through changes in the fluence, intensity, angle of incidence and/or the plane of polarization.

3. The method of claim 1, wherein the nanopost array mask pattern arrangement is generated by computer aided design.

4. The method of claim 1, wherein the sample is deposited onto the columnar structures.

5. The method of claim 1, wherein the array is adapted to be in cooperative association with a laser having a specific wavelength wherein the periodicity of the nanopost is commensurate with the specific wavelength of the laser.

6. The method of claim 1, wherein the sample is selected from the group consisting of pharmaceuticals, dyes, explosives, narcotics, polymers, single cells, small cell populations, cell cultures, tissue samples, and biomolecules.

7. The method of claim 1, wherein the sample is a microorganism selected from the group consisting of unicellular eukaryotes, prokaryotes, viruses, and any combination thereof.

8. A method for the direct chemical analysis of a nanopost-deposited sample by mass spectrometry, comprising the steps of:
- (a) depositing the sample onto a silicon nanopost array, wherein said silicon nanopost array is prepared by a process comprising:
  - (i) generating a nanopost array mask pattern arrangement having a nanopost diameter of about 50 nm to about 800 nm and a periodicity of from about 100 nm to about 1600 nm;
  - (ii) writing said mask pattern onto a substrate comprising silicon or semiconductor material, to produce processed areas that are covered with columnar structures having said diameter and said periodicity; and
  - (iii) developing said columnar structures to produce columnar structures comprising a height of about 100 nm to about 2000 nm;
- (b) subjecting the sample to laser desorption ionization using a photonic ion source; and
- (c) analyzing the produced ions using mass spectrometry.

9. The method of claim 8, further comprising the step of controlling ion production and molecular fragmentation by varying laser radiation properties through changes in the fluence, intensity, angle of incidence and/or the plane of polarization.

10. The method of claim 8, wherein the nanopost array mask pattern arrangement is generated by computer aided design.

11. The method of claim 8, wherein the sample is deposited onto the columnar structures.

12. The method of claim 8, wherein the array is adapted to be in cooperative association with a laser having a specific wavelength wherein the periodicity of the nanopost is commensurate with the specific wavelength of the laser.

13. The method of claim 8, wherein the sample is selected from the group consisting of pharmaceuticals, dyes, explosives, narcotics, polymers, single cells, small cell populations, cell cultures, tissue samples, and biomolecules.

14. The method of claim 8, wherein the sample is a microorganism selected from the group consisting of unicellular eukaryotes, prokaryotes, viruses, and any combination thereof.

15. The method of claim 8, wherein in step (a)(iii), said columnar structures are developed using reactive ion etching with a dopant-containing etching gas.

16. The method of claim 8, wherein the dopant-containing etching gas contains fluorine atoms.

17. The method of claim 15, wherein the dopant-containing etching gas is $C_4F_8$, $SF_6$, or a combination thereof.

* * * * *